US008673311B2

(12) United States Patent
Cutting et al.

(10) Patent No.: US 8,673,311 B2
(45) Date of Patent: Mar. 18, 2014

(54) BACTERIAL SPORE HAVING THERAPEUTIC AGENT ADSORBED ON ITS SURFACE

(75) Inventors: Simon Michael Cutting, Egham-Surrey (GB); Hong Anh Huynh, Egham-Surrey (GB)

(73) Assignee: Royal Holloway and Bedford New College (GB)

( * ) Notice: Subject to any disclaimer, the term of this patent is extended or adjusted under 35 U.S.C. 154(b) by 0 days.

(21) Appl. No.: 13/497,169

(22) PCT Filed: Sep. 21, 2010

(86) PCT No.: PCT/GB2010/001771

§ 371 (c)(1), (2), (4) Date: Jun. 6, 2012

(87) PCT Pub. No.: WO2011/033275

PCT Pub. Date: Mar. 24, 2011

(65) Prior Publication Data

US 2012/0237544 A1 Sep. 20, 2012

(30) Foreign Application Priority Data

Sep. 21, 2009 (GB) .................................. 0916570.5

(51) Int. Cl.

| | |
|---|---|
| ***A61K 35/74*** | (2006.01) |
| ***A61K 39/008*** | (2006.01) |
| ***A61K 39/04*** | (2006.01) |
| ***A61K 39/05*** | (2006.01) |
| ***A61K 39/07*** | (2006.01) |
| ***A61K 39/095*** | (2006.01) |
| ***A61K 39/102*** | (2006.01) |
| ***A61K 39/108*** | (2006.01) |
| ***A61K 39/112*** | (2006.01) |
| ***A61K 39/118*** | (2006.01) |
| ***A61K 39/12*** | (2006.01) |
| ***A61K 39/29*** | (2006.01) |

(52) U.S. Cl.

USPC .................. 424/184.1; 424/93.41; 424/93.46; 424/208.1; 424/209.1; 424/224.1; 424/226.1; 424/227.1; 424/229.1; 424/234.1; 424/241.1; 424/245.1; 424/246.1; 424/248.1; 424/249.1; 424/256.1; 424/257.1; 424/258.1; 424/269.1; 424/272.1

(58) Field of Classification Search

CPC ..... A61K 35/74; A61K 39/015; A61K 39/07; A61K 39/08; A61K 39/385; A61K 2039/542

See application file for complete search history.

(56) References Cited

U.S. PATENT DOCUMENTS 4,578,270 A * 3/1986 Csizer et al. ............... 424/203.1
6,979,449 B1 * 12/2005 Mock ......................... 424/246.1

FOREIGN PATENT DOCUMENTS

WO 02/00232 A2 1/2002
WO 03/055513 A2 7/2003
WO 2010/006326 A2 1/2010

OTHER PUBLICATIONS

Hoang et al. Recombinant *Bacillus subtilis* expressing the *Clostridium perfringens* alpha toxoid is a candidate orally delivered vaccine against necrotic enteritis. Infection and Immunity, 2008, vol. 76, p. 5257-5265.*

Janado et al. Effect of salt in the inter- and intramolecular hydrophobic interactions of macromolecules. Journal of Solution Chemistry, 1986, vol. 15, p. 839-850.*

Duc et al: "Immunization Against Anthrax Using *Bacillus subtilis* Spores Expressing the Anthrax Protective Antigen", Vaccine, Elsevier LTD, GB vol. 25, No. 2, Dec. 8, 2006, p. 346-355, XP005798950.

Jendrek Scott et al: "Evaluation of the Compatibility of a Second Generation Recombinant Anthrax Vaccine With Aluminum-Containing Adjuvants.", Vaccine, vol. 21, No. 21-22, Jun. 20, 2003, p. 3011-3018, XP002613043.

International Serach Report for PCT/GB2010/001771 Dated Dec. 21, 2010.

* cited by examiner

*Primary Examiner* — Louise Humphrey

(74) *Attorney, Agent, or Firm* — Banner & Witcoff, Ltd.

(57) ABSTRACT

The present invention relates to a method of coating a spore with one or more therapeutic agents. The present invention also relates to a coated spore obtained by the method of the present invention and the use of the coated spore as a vaccine.

22 Claims, 24 Drawing Sheets

BACTERIAL SPORE HAVING THERAPEUTIC AGENT ADSORBED ON ITS SURFACE

Figure 1A:
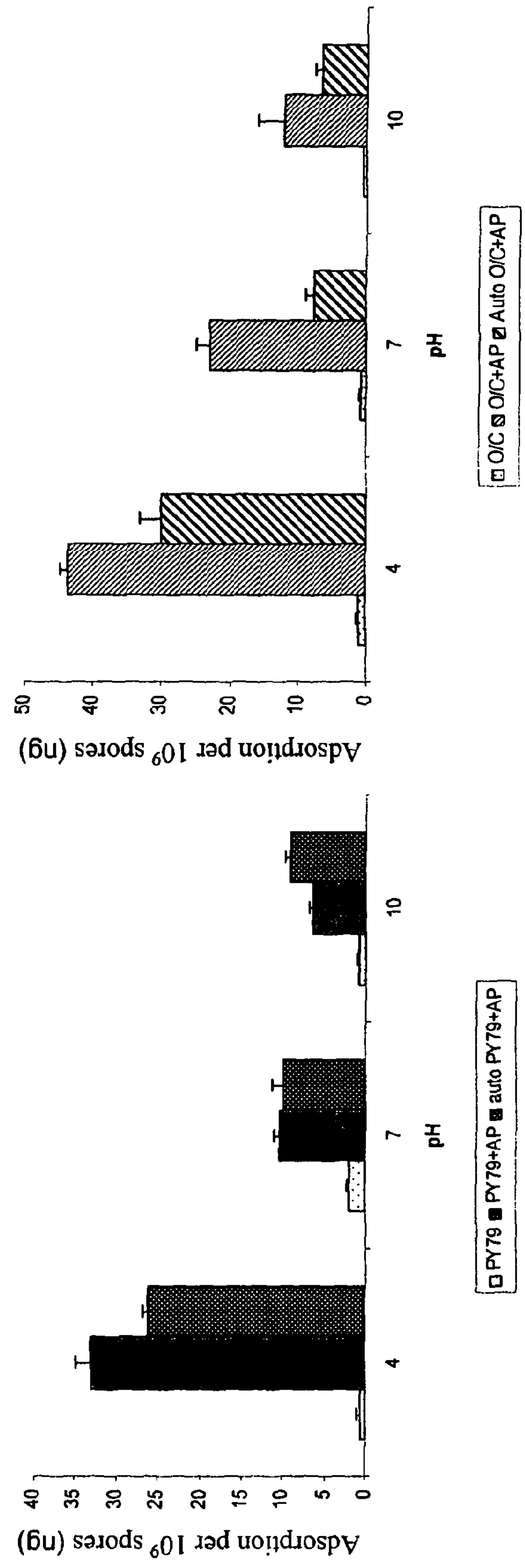

The present invention relates to a method of coating a spore with one or more therapeutic agents. The present invention also relates to a coated spore obtained by the method of the present invention and the use of the coated spore as a vaccine.

The development of new-generation vaccines has followed a number of strategic avenues including the use of live recombinant bacteria. Of these, the use of genetically engineered bacterial spores has been shown to offer promise as both a mucosal as well as a heat-stable vaccine delivery system. Spores of the genus *Bacillus* are currently in widespread use as probiotics enabling a strong case to be made for their safety.

The use of live bacteria as vaccine delivery systems has provided one arm in the push to develop new and more effective vaccines. Live bacterial vaccines include a number of species including those of *Salmonella, Shigella, Escherichia coli, Lactobacillus* and *Bacillus* (Detmer et al., 2006). In some cases the strategy used is to exploit the life cycle of a pathogen, for example, one oral dose of recombinant, attenuated, *Salmonella enterica* serovar Typhi Ty21a is sufficient to generate a potent immune response because the bacterium efficiently targets the gut-associated lymphoid tissue (GALT) (Bumann et al., 2000). Furthermore, *Bacillus subtilis* engineered to express heterologous antigens on the surface of the spore or within the germinating spore can be used for oral or nasal delivery of antigens and confer protective immunity. The *B. subtilis* spore, as a dormant life form, has further advantages of being heat-stable, non-pathogenic and in current use in humans and animals as a probiotic (Hong et al., 2005). Recombinant spores expressing protective antigens from *Clostridium tetani* (Duc et al., 2003), *Clostridium perfringens* (Hoang et al., 2008), *Bacillus anthracis* (Duc et al., 2007) as well as the parasite *Clonorchis sinensis* (Zhou et al., 2008) have all been shown to confer protection using animal models. On the other hand the use of recombinant bacteria also raises concerns over the use of genetically-modified microorganisms (GMOs) and clearance of the bacterium from the host following delivery (Detmer et al., 2006).

A second goal in the development of better vaccines is in identifying new adjuvants that can boost immunogenicity of otherwise, weakly immunogenic antigens (e.g., recombinant protein subunits and synthetic peptides). Currently, only one adjuvant, alum, is licensed for human use yet a battery of potential vaccine adjuvants are under development including immunostimulatory adjuvants, mucosal adjuvants, lipid particles and particulate adjuvants (Singh et al., 1999 and Moyle et al., 2004). Each of these have their strengths but also weaknesses. One of the new classes of adjuvants, referred to as particulate adjuvants (e.g., liposomes, virosomes, virus-like particles, poly-lactide-co-glycolide (PLG) microspheres and immune stimulating complexes (ISCOMS)), are particularly encouraging because they mimic the pathogens the immune system has evolved to destroy. Particulate adjuvants efficiently target antigen presenting cells (APCs) and once internalised within the cell are processed by the class I and class II MHC (major histocompatibility complex) pathways leading to antigen presentation on the surface of the APC. Biodegradable PLGs have been shown to induce CTL responses; a prerequisite for combating intracellular pathogens (Maloy et al., 1994). Studies on copolymer adjuvants have shown that for induction of a broad range of immune responses (antibody and cell-mediated) it is necessary that the antigen remains in its native form (Hunter et al., 2002). Many antigens prepared in water-in-oil emulsions are rapidly engulfed by APCs, degraded, and then enter the class II pathway leading to antibody production but in a challenge model, fail to protect. This is thought to be due to the failure to produce the IgG2a isotype that is important for recognition of conformational epitopes (Hunter et al., 2002). Stabilisation of antigens on inert surfaces in their native form coupled with the ability to induce potent immune responses remain one of the challenges in vaccine and adjuvant formulations.

International Patent Application WO 03/055513 and Malkiel et al., 1971 discloses the use of spores from *Bacillus subtilis* in combination with an antigen; however, there is no disclosure of coating the spores with the antigen.

The present invention provides a method of adsorbing a therapeutic agent onto a bacterial spore comprising:

mixing the spores and the therapeutic agent at a pH that is less than or equal to the isoelectric point of the therapeutic agent.

It has been found that by mixing the spores and the therapeutic agent under such conditions that the therapeutic agent is adsorbed onto the spores. It has been determined that the negatively charged, yet hydrophobic, surface of bacterial spores can be used for binding therapeutic agents, such as antigens. The therapeutic agent binds to the spore surface while maintaining its native conformation and function. In particular, it has been found that when antigens are adsorbed onto the spore that a strong immune response is generated (i.e., a Th1 and a Th2 response).

In order for the therapeutic agent to be adsorbed, the spores and therapeutic agent only need to be in contact for a few minutes; however, preferably the spores and therapeutic agent are in contact for about 10 or more minutes.

The term “adsorbing”, also referred to herein as coating, refers to the non-covalent binding of the therapeutic agent to the surface of the spore.

The spore can be any suitable bacterial spore including *Bacillus* and *Clostridia* spores. Preferably the spore is a probiotic spore. It is particularly preferred that the spore is a *Bacillus* spore, such as a *B. subtilis* or *B. clausii* spore. The spore may be a genetically engineered spore that has been engineered to express one or more therapeutic agents on its surface. Preferably the spore has not been engineered to express one or more therapeutic agents on its surface. Particularly preferred spores include the spores of *B. subtilis* strain PY79, *B. subtilis* strain HU58 (Tam et al., 2006), *B. subtilis* strain HT251 (isogenic to strain PY79 and carries a recombinant gene on its genome that expresses a modified spore coat protein, CotB, that has been fused to GST-$Cpa_{247-370}$ (Hoang et al., 2008)), *B. subtilis* strain RH103 (expresses the immunogen, TTFC (tetanus toxin fragment C) from *Clostridium tetani* on the spore surface as a chimera fused to the CotB protein (Isticato et al., 2001)) and *B. clausii* strain O/C. Most preferably the spore is that produced by *B. subtilis* strain PY79.

The spore is preferably denatured (i.e., inactivated) so that germination, and thus subsequent proliferation, is prevented. Numerous methods for denaturing spores are known to those skilled in the art including, autoclaving, UV irradiation, gamma irradiation, and genetically modifying the spore. Preferably the spore is denatured by autoclaving.

The therapeutic agent can be any suitable therapeutic agent including proteins such as antigens, enzymes (e.g., that promote or enhance digestion such as cellulases, lipases, amylases, etc.), antibody molecules, anticancer proteins (e.g., herceptin, p53, etc.) and other therapeutic proteins (e.g., labile toxin from ETEC (enterotoxigenic *E. coli*), cholera toxin subunit B, tetanus toxoid, etc.); denatured viruses or other infectious agents, such as HIV, Hepatitis A, Hepatitis B, influenza viruses (orthomyoxvirus), Herpes viruses, papovaviruses, Rhaboviruses, vesicular stomatitis virus (VSV), etc); small chemical molecules such as anti-cancer agents (e.g., taxol), markers, receptor agonists and receptor antagonists. The term "therapeutic agent" includes both active agents that directly treat a disease or disorder and prophylactic agents that prevent the development or progression of a disease or disorder (e.g., vaccine antigens). Preferably the therapeutic agent is an antigen. Suitable antigens include proteins or peptides derived from an infectious agent, tumour antigens and allergens.

The infectious agent may be prokaryotic, eukaryotic, prion, or viral. Suitable infectious viruses include HIV, Hepatitis A, Hepatitis B, influenza viruses (orthomyoxvirus), Herpes viruses, papovaviruses, Rhabdoviruses, vesicular stomatitis virus (VSV), etc. Suitable infectious bacteria include *Escherichia* spp. (e.g., *E. coli* and ETEC (enterotoxigenic *E. coli*)), *Legionella* spp., *Bacillus* spp., *Neisseria* spp., *Haemophilus* spp., *Helicobacter* spp., *Corynebacterium* spp., *Pneumococcus* spp., *Salmonella* spp., *Mycobacterium* spp., *Chlamydia* spp. and *Shigella* spp. (e.g., *S. dysenteriae, S. sonnei* and *S. flexneri*), etc. Suitable parasites include *Cryptosporidium* spp., *Toxoplasma* spp., *Leishmania* spp., *Theilera* spp. etc. and any parasites with an intracellular stage in their lifecycle, e.g., *Plasmodium* spp.

The tumour antigen may be any tumour antigen. Numerous tumour antigens are known to those skilled in the art. Examples of tumour antigens include B7, CEA, ESO1, Her2, Muc-1, OFA-iLRP (oncofetal antigen immature laminin receptor protein), etc.

The allergen may be any allergen known to those skilled in the art. Examples of allergens include grass pollen (e.g., Ph1 p 5b), tree pollen (e.g., Bet v1), house dust mite (e.g., Der p1), animal dander (e.g., cat Fel d1), moulds, latex, food allergens (e.g., peanut Ara h2, chicken egg ovalbumin and ovamucoid) and bee/wasp venom (e.g., phospolipase A2).

A plurality of different therapeutic agents may be adsorbed onto the spore. For example, different antigens can be adsorbed onto the spore to provide immune protection against a number of different diseases. When several different antigens are adsorbed onto the spore the antigens can be conjugated to each other. Furthermore, adjuvants can be adsorbed onto the spore. Suitable adjuvants include cholera toxin subunit B (CTB) and heat-labile enterotoxin (LTB). Other adjuvants, including Th1 adjuvants (i.e., an adjuvant that preferentially potentiates a Th1 immune response) are well know to those skilled in the art. See in particular International Patent Application WO 99/58683, which describes a number of suitable adjuvants.

The therapeutic agent may be linked to a modifying agent. Suitable modifying agents include agents that enhance the adsorption of the therapeutic agent to the spore or improve the conformational stability of the therapeutic agent. Such agents include glutathione S-transferase (GST), 20 lipoprotein D from *Haemophilus influenzae*, maltose binding protein, beta-galactosidase and chaperones. Moreover, the modifying agent may act as an adjuvant in the sense of providing a generalized stimulation of the immune system of the organism receiving the protein.

The term "mixing" means that the spore and therapeutic agent are placed in contact with each other so that the therapeutic agent can be adsorbed onto the surface of the spore. Preferably, the spore and therapeutic agent are mixed by continuous agitation.

The therapeutic agent and the spore are mixed together at a pH that is less than or equal to the isoelectric point of the therapeutic agent. The isoelectric point of the therapeutic agent can be determined using a variety of standard techniques. It is particularly preferred that the mixing pH is less than the isoelectric point of the therapeutic agent. It is preferred that the pH is less than 7, more preferably less than 5 and most preferably about 4 or less. It is also preferred that the pH during mixing is less than the isoelectric point of the therapeutic agent and above the Zero Point of Charge (ZPC) of the spore, i.e., so that the spore is negatively charged at the mixing pH. For *B. subtilis* spores the ZPC is around 2, and therefore the mixing pH is preferably above pH 2.

It is also preferred that the spore and the therapeutic agent are mixed under conditions where the hydrophobic and electrostatic interactions between the spores and the therapeutic agent are enhanced. Depending on the spore and therapeutic agent used, different salt concentrations may promote electrostatic or hydrophobic interactions, i.e., binding. The optimum salt concentrations will need to be determined for particular spore and therapeutic agent combinations. Basically, low salt concentrations generally favour electrostatic interactions. Thus a protein, which is predominantly bound by electrostatic interactions will bind better at a low salt concentration. A high salt concentration generally favours hydrophobic interactions. Thus, therapeutic agents that are predominantly bound by hydrophobic interactions will bind better at a high salt concentration. A low salt concentration is defined as a salt concentration less than 0.3M, more preferably less than 0.15M and most preferably less than 0.05M. A high salt concentration is defined as a salt concentration that is 0.3M or greater and preferably 0.8M or greater.

In a specific embodiment of the present invention, the spore and a therapeutic agent predominantly bound by electrostatic interactions (e.g. a protein) are mixed together in a binding solution, wherein the pH of the binding solution is less than or equal to the isoelectric point of the therapeutic agent and has a salt concentration of less than 0.3M. The binding solution may be a PBS buffer or any other suitable solution.

In one embodiment of the invention the method additionally comprising formulating the spores with the adsorbed therapeutic agent as a pharmaceutical composition by combining with one or more pharmaceutically acceptable carriers or vehicles. The pharmaceutical composition can be formulated as an immunogenic composition or a vaccine composition. When the pharmaceutical composition is formulated as an immunogenic composition or a vaccine composition, the method may additionally comprise adding an adjuvant to the composition. The present invention also provides an immunogenic composition or a vaccine composition obtained by such a method. Preferably the immunogenic composition or the vaccine composition, comprise one or a more antigens derived from one or more infectious agents. The present invention also provides the immunogenic composition or the vaccine composition for use in raising a protective immune response against the one or more infectious agents. The present invention also provides a method of raising a protective immune response in an individual against one or more infectious agents, comprising administering an effective amount of the immunogenic composition or the vaccine composition comprising one or more antigens derived from the one or more infectious agents.

The present invention also provides a bacterial spore having one or more therapeutic agents adsorbed on its surface obtained by the method of the present invention.

The present invention also provides a bacterial spore having one or more therapeutic agents adsorbed on its surface, and obtained by the method of the present invention, for use in therapy. The type of therapy will depend on the therapeutic agent adsorbed on the spore. For example, if an antigen is adsorbed on the spore, then it can be used to raise an immune response against the infectious agent from which the antigen has been derived. Alternatively, if an anti-cancer agent is adsorbed on the spore, it can be used to treat cancer.

In a particular embodiment of the present invention there is provided the use of a spore having one or more antigens adsorbed on its surface, and obtained by the method of the present invention, to raise a protective immune response in an individual against the one or more antigens.

The present invention also provides a method of raising a protective immune response in an individual against an antigen comprising administering an effective amount of a spore having the antigen adsorbed on its surface by the method of the present invention.

In a further preferred embodiment of the present invention a spore having one or more antigens adsorbed on its surface and obtained by the method of the present invention is provided for use as a vaccine.

It has been shown that using the present method spores having antigens adsorbed on their surface can confer protection to a number of different pathogens. A broad range of immune responses was induced indicating that the antigens can bind to the spore surface while maintaining their native conformation. The inventors have determined that the negatively charged and hydrophobic surface layer of spores provides a suitable platform for adsorption of therapeutic agents, e.g., protein antigens.

Remarkably, killed or inactivated spores appear at least as effective as live spores. In fact inactivated spores appear to be more effective than live spores. The spore appears to present a bound antigen in its native conformation promoting a cellular (Th1-biased) response coupled with a strong antibody response. The broad spectrum of immune responses elicited coupled with the attendant benefits of safety indicate that spore adsorption is appropriate for improving the immunogenicity of antigens as well as the delivery of other therapeutic molecules.

The coated spores obtained by the method of the present invention can be administered in combination with any other suitable therapeutic agents, such as interferons, cytokines, etc. that may further improve the therapeutic response.

The present invention also provides a pharmaceutical composition comprising the coated spores obtained by the method of the present invention and any pharmaceutically acceptable carrier or vehicle. Suitable pharmaceutically acceptable carriers and vehicles are well known to those skilled in the art.

The pharmaceutical compositions of this invention may be administered in any suitable manner including orally, parenterally, mucosally (oral, nasal, rectal) and sublingually. When administering the coated spores orally, it is preferred that they are coated with a suitable coating to protect the adsorbed therapeutic agent from degradation. Preferably the coated spores are administered mucosally or parenterally. The term parenterally includes subcutaneous, intracutaneous, intravenous, intramuscular, intra-articular, intrasynovial, intrasternal, intrathecal, intralesional and intracranial injection or infusion techniques.

Formulations suitable for parenteral administration include aqueous and non-aqueous sterile injection solutions which may contain anti-oxidants, buffers, bacteristatic compounds and solutes which render the formulation isotonic with the bodily fluid, preferably the blood, of the individual; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. Furthermore, the sterile injectable preparation may be a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant or a similar alcohol.

The pharmaceutical composition of the invention may also include adjuvant systems for enhancing the immunogenicity of the composition. Preferably the adjuvant system raises preferentially a Th1 type of response.

The pharmaceutical compositions of this invention may be administered mucosally by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The dose at which the coated spores of the invention are administered to an individual will depend upon a variety of factors such as the age, weight and general condition of the individual, the condition that is being treated and the route by which the coated spores are being administered. A suitable dose may however be $10^5$ to $10^{11}$ spores per dose. If doses in this range are not sufficient, the dose may be increased. Those skilled in the art will recognise the appropriate dosage level to test, from research reported herein. However, by way of guidance only, for administration to mammals, and particularly humans, it is expected that the daily dosage level of an active agent will be from 0.01 mg/kg to 10 mg/kg, typically around 1 mg/kg. The above dosages are exemplary of the average case. There can, of course be individual instances where higher or lower dosage ranges are merited, and such are within the scope of this invention.

The dosage range required depends on the choice of spore and adsorbed therapeutic agent, the route of administration, the nature of the pharmaceutical formulation, the nature of the subject's condition, and the judgment of the attending practitioner.

A vaccine composition is conveniently in injectable form. Conventional adjuvants may be employed to enhance the immune response. A suitable unit dose for vaccination is 0.5-5 microgram/kg of antigen, and such dose is preferably administered 1 to 3 times and with an interval of 1 to 3 weeks. With the indicated dose range, no adverse toxicological effects will be observed with the compounds of the invention which would preclude their administration to suitable individuals.

Wide variations in the needed dosage, however, are to be expected in view of the variety of therapeutic agents and the differing efficiencies of various routes of administration. For example, oral administration would be expected to require higher dosages than administration by intravenous injection. Variations in these dosage levels can be adjusted using standard empirical routines for optimization, as is well understood in the art.

The present invention is now described by way of example only with reference to the following figures.

Figure 1B:
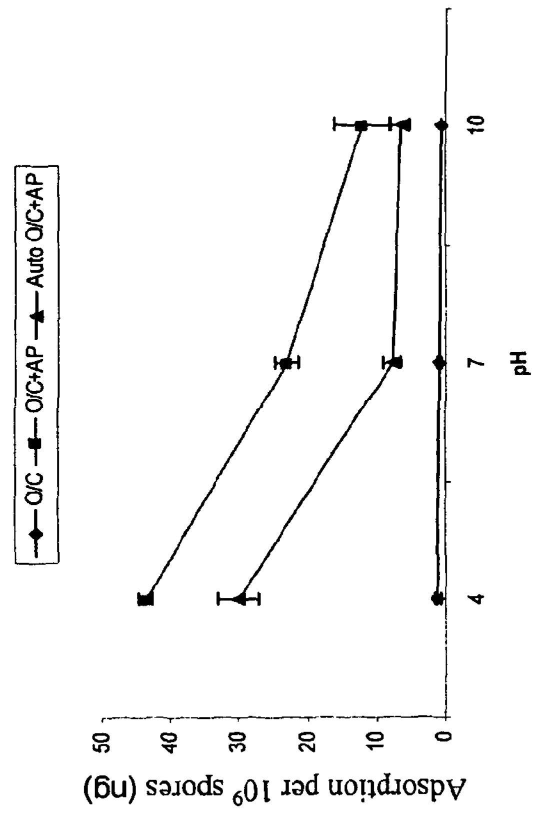
Figure 1B:
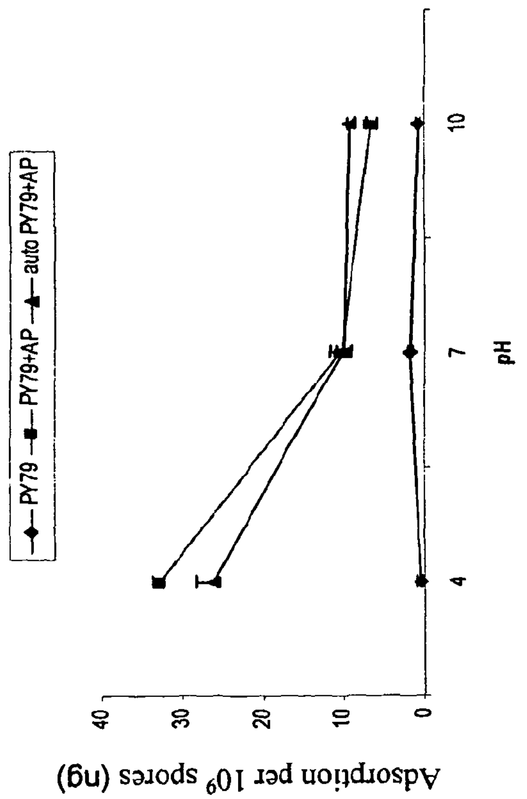

FIG. 1 shows that the adsorption of alkaline phosphatase (AP) enzyme is affected by pH. Saturated AP was adsorbed in a 200 μl suspension of $2\times10^9$ spores (PY79, O/C, autoclaved PY79 and O/C spores) in binding buffer (PBS pH4, pH7 and pH10, respectively) at RT (room temperature) for 45 minutes. The mixtures were washed 3 times with the same buffer and then the pellets were collected and resuspended in 100 μl of substrate (pNPP). OD (405 nm) of the supernatant was measured after 45 minutes. The amount of AP adsorbed on spores was converted from OD values based on the reference of AP activity.

Figure 2:
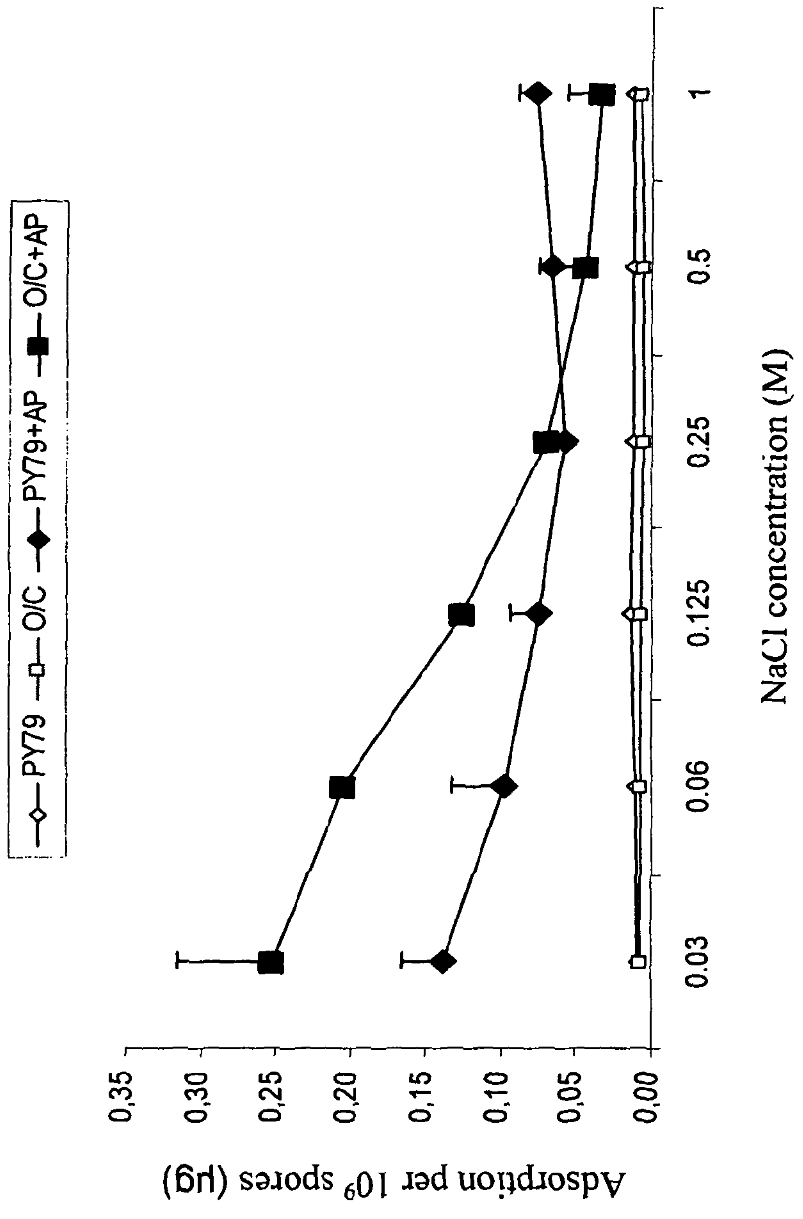

FIG. 2 show the effect of NaCl concentration on adsorption of alkaline phosphatase on spores. Saturated AP was adsorbed on $2\times10^9$ spores (*B. subtilis* PY79, *B. clausii* O/C) in 200 μl of binding buffer (pH4) containing different concentrations of NaCl (0.03M, 0.06M, 0.125M, 0.25M, 0.5M and 1M, respectively), at RT for 45 minutes. The mixtures were washed 3 times with the same buffer and then the pellets were resuspended in 100 μl of substrate (pNPP). OD (405 nm) of supernatant were measured after 45 minutes. The amount of AP adsorbed on spores was converted from OD values based on the reference of AP activity.

Figure 3A:
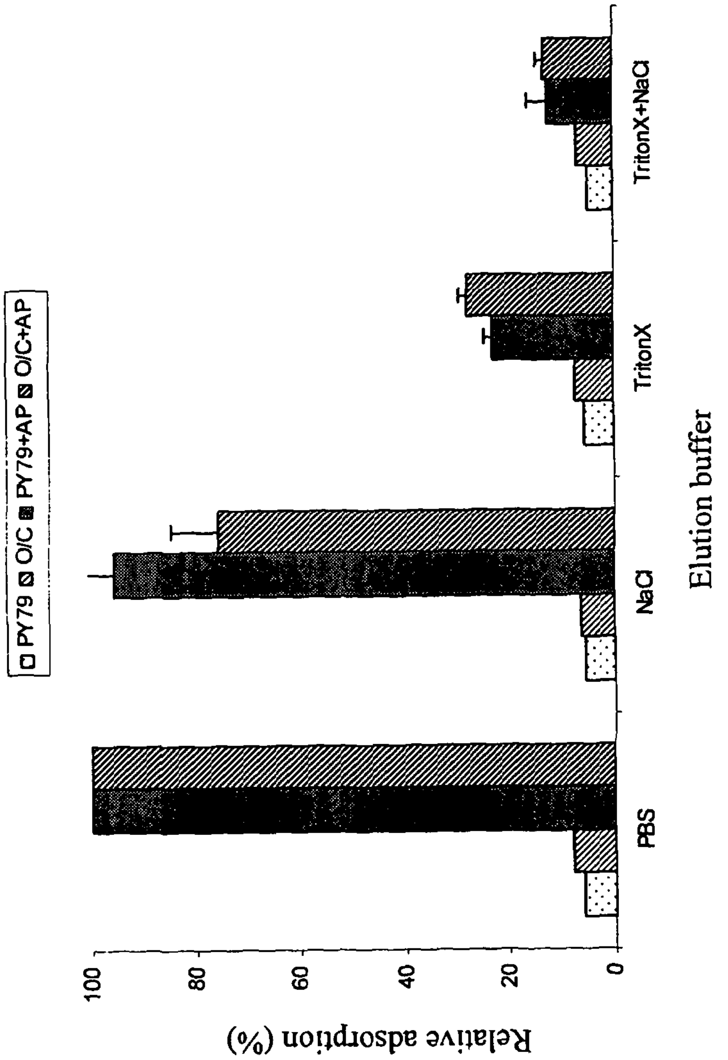
Figure 3B:
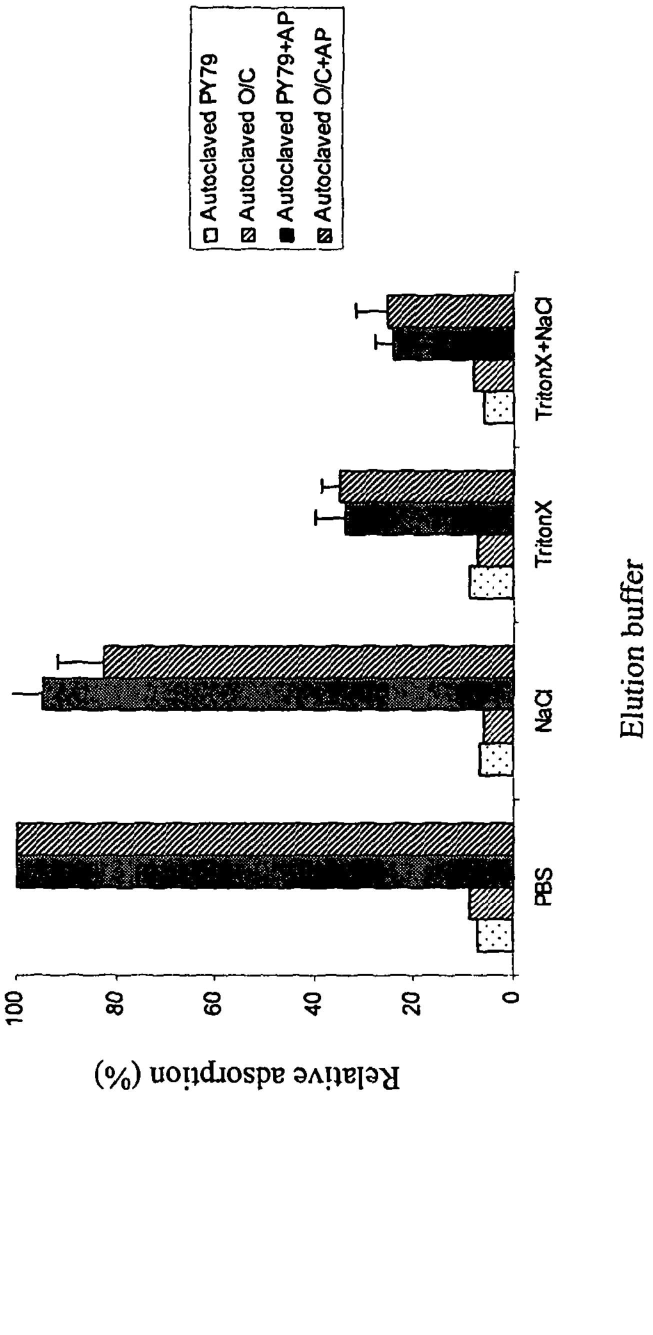

FIG. 3 shows the dissociation of alkaline phosphatase from adsorbed spores by different elution buffers. Saturated alkaline phosphatase was adsorbed on $2\times10^9$ spores (PY79, O/C and autoclaved PY79, O/C spores) in 200 μl of binding buffer (PBS, pH4) for 45 min at RT. Then spores were washed 3 times with the same buffer and washed 1 time with different elution buffer (PBS pH4, PBS+1M NaCl, PBS+1% TritonX, PBS+1MNaCl+1% TritonX, PBS+Octyl β-D-Glucopyranoside, PBS+Octyl β-D-Glucopyranoside+1M NaCl), and followed by washing 1 time with PBS. The pellets were collected by centrifuging and re-suspended in 100 μl of pNPP substrate. The OD of the supernatant was measured at 405 nm after 45 minutes. The percentages of retained AP on spores were calculated by comparing with amount of AP on spores washed with binding buffer only (PBS pH4). Note: Activity of AP validated in different buffers was similar.

Figure 4:
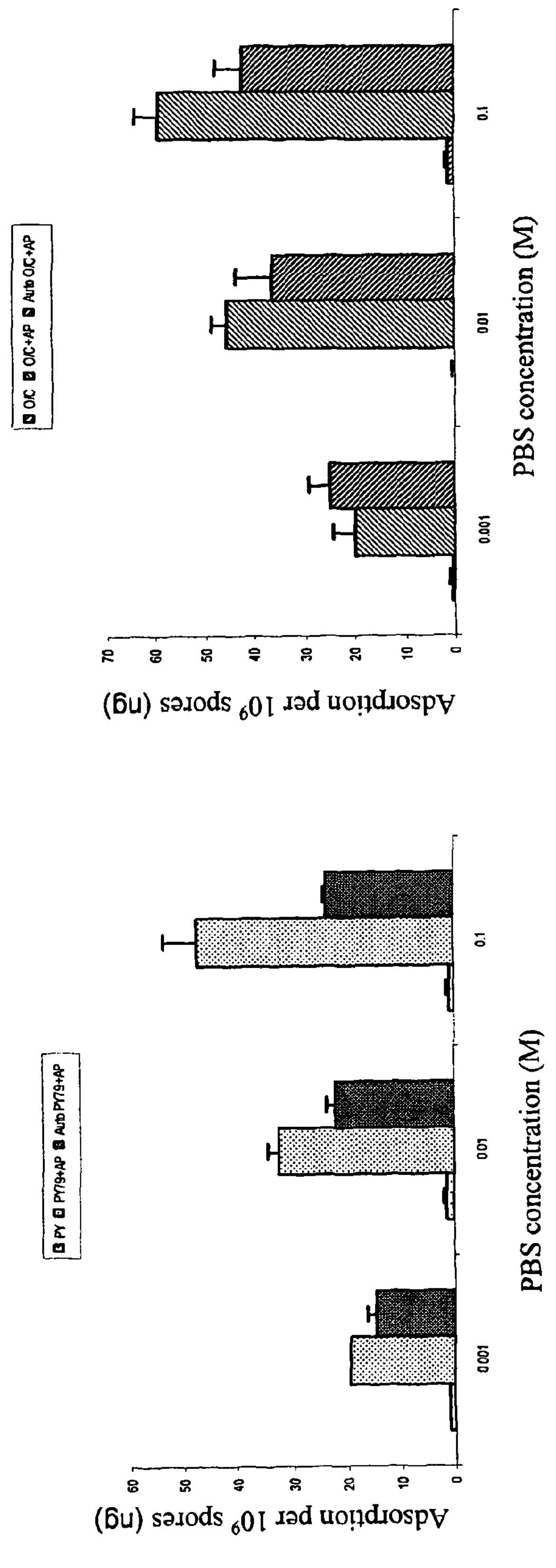

FIG. 4 shows the effect of PBS concentration on adsorption of alkaline phosphatase on spores. Saturated AP was adsorbed on $2\times10^9$ spores (PY79, O/C) in 200 μl of binding buffer (PBS pH4 0.001M, 0.01M, 0.1M respectively), at RT for 45 minutes. The mixtures were washed 3 times with the same buffer and then the pellets were resuspended in 100 μl of substrate (pNPP). OD (405 nm) of supernatant was measured after 45 minutes. The amount of AP adsorbed on spores was converted from OD values based on the reference of AP activity.

Figure 5:
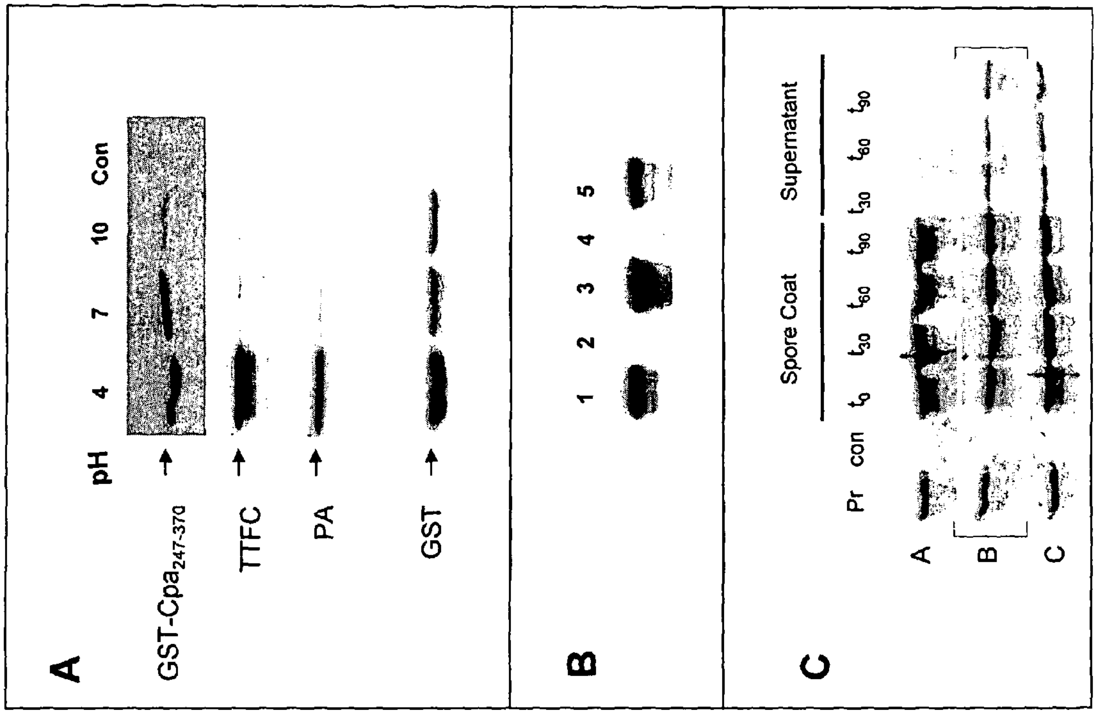

FIG. 5 shows the adsorption of immunogens to spores.

Panel A: Purified suspensions of PY79 spores in different pH buffers (PBS) were mixed with purified recombinant protein (2 μg) for 1 h at RT. Spores were centrifuged, washed two times and coat proteins extracted. Using one tenth of the extraction western blotting of size-fractionated proteins was used for detection. In each case one predominant band was detected which is shown in the figure. 0.1 μg of purified recombinant protein is shown for comparison. The control lane (Con) shows the corresponding blot from spores taken through the entire procedure without protein.

Panel B: Binding of 2 μg TTFC to spore coats as described in Panel A. Lane 1, 0.1 μg of TTFC as a control; lane 2, unbound PY79 spores; lane 3, PY79 spores+TTFC; lane 4, unbound autoclaved PY79 spores; lane 5, autoclaved PY79 spores+TTFC.

Panel C: Suspensions of spores ($2\times10^9$ c.f.u. (colony forming units)) were centrifuged and resuspended in 0.2 ml of PBS at pH 4. Purified recombinant TTFC protein (2 μg) was added to the spore suspension and the binding mixture incubated for 1 h at RT. Spores were centrifuged and the pellet washed two-times with PBS at pH4. The washed pellet was next resuspended in 200 μl of PBS at either pH4 (lane A), pH 7 (lane B) or pH 10 (lane C). At indicated time points (30, 60 and 90 min), spores were centrifuged and the supernatants saved and one twentieth loaded onto a 12% SDS-PAGE gel. Pellets were resuspended in 100 μl of spore coat extraction buffer, incubated at 68° C. for 1 h to remove spore coat proteins from spores and one tenth loaded onto a 12% SDS-PAGE gel. For controls 0.1 μg of the recombinant protein was run on the gel.

Figure 6:
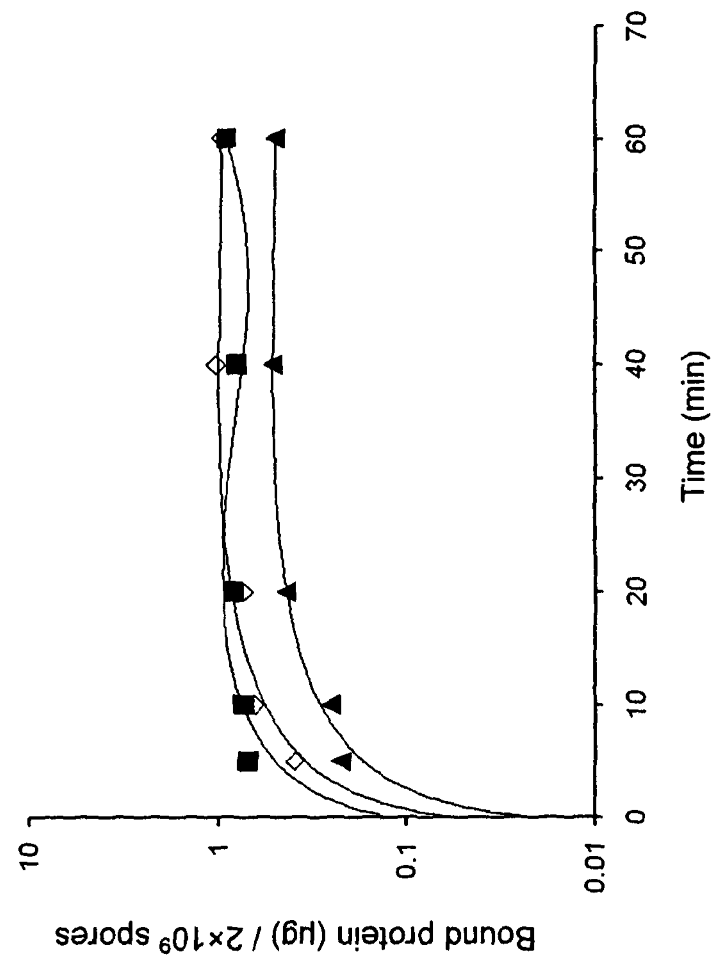

FIG. 6 shows the kinetics of adsorption. Suspensions of spores ($2\times10^9$ cfu) were mixed with 10 μg of recombinant protein in PBS (pH 4) and incubated at RT and samples taken thereafter. Spores were washed two-times with PBS (pH 4). ○, TTFC+PY79 spores; ▲, GST-$Cpa_{247-370}$+PY79 spores; ■, PA+HU58 spores.

Figure 7:
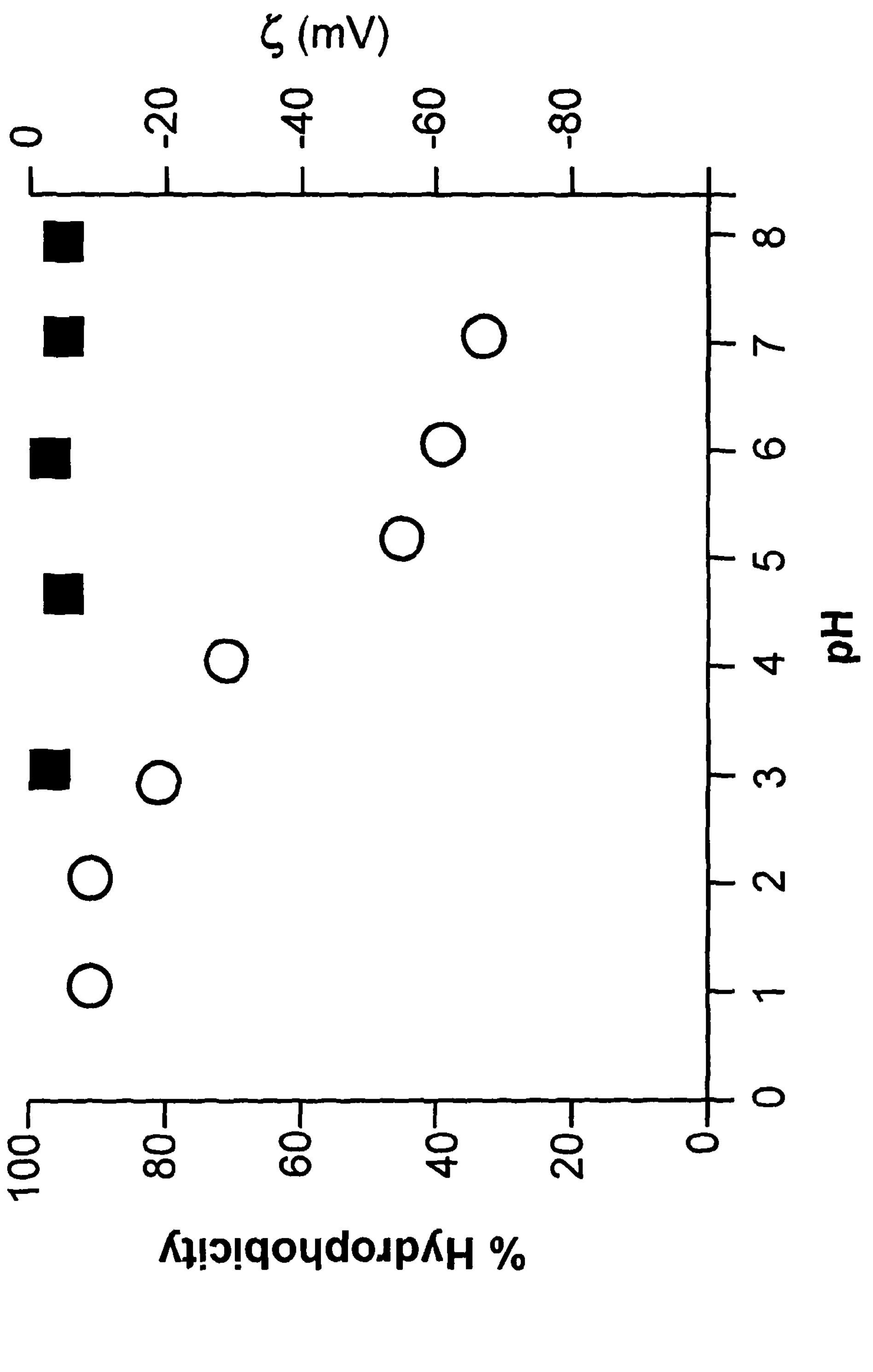

FIG. 7 shows the electro kinetics and hydrophobicity of *B. subtilis* PY79 spores. Zeta potential measurements (○) of purified suspensions of PY79 spores in water between pH 1 and 12. Hydrophobicity (■) of PY79 spores determined by the SATH assay in the pH range of 3-8.

Figure 8:
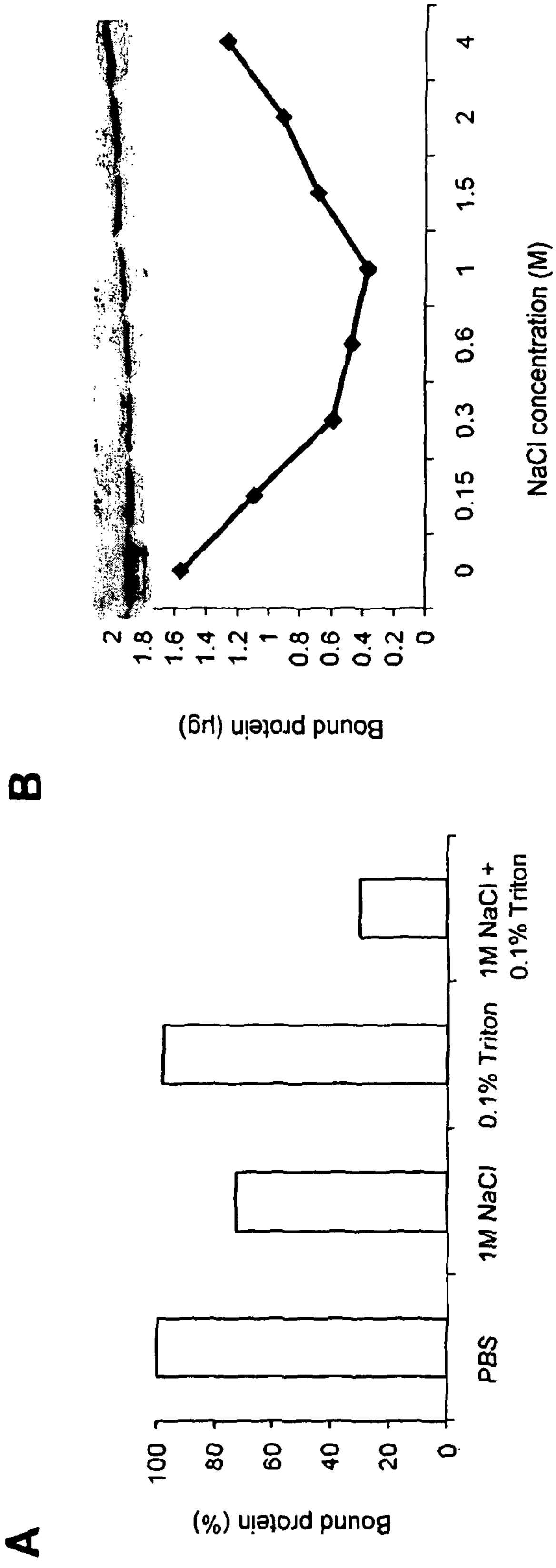

FIG. 8 shows the ionic and hydrophobic properties of protein adsorption.

Panel A: Recombinant TTFC (10 μg) was mixed with purified suspensions of PY79 spores ($2\times10^9$ cfu) in 0.2 ml PBS (pH 4, 0.15M) for 1 h at RT. After two washes with PBS, the pellet was resuspended in pH 4 PBS, 1M NaCl, 0.1% Triton X-100, or 1M NaCl+0.1% Triton X-100 and incubated at RT for 15 min followed by two washes with the same buffer used for resuspension after which coat proteins were extracted. The data showed are the percentage of remaining bound protein.

Panel B: Purified recombinant TTFC (10 μg) was mixed with purified suspensions of PY79 spores ($2\times10^9$ cfu) in 0.2 ml PBS (pH 4) containing different concentrations of NaCl (0-4 M). All the binding mixtures were incubated at RT for 1 hour. Spores were centrifuged, washed two times in the PBS buffer containing the same NaCl concentration and coat proteins extracted and displayed as the total amount of protein extracted/$2\times10^9$ spores.

Figure 9:
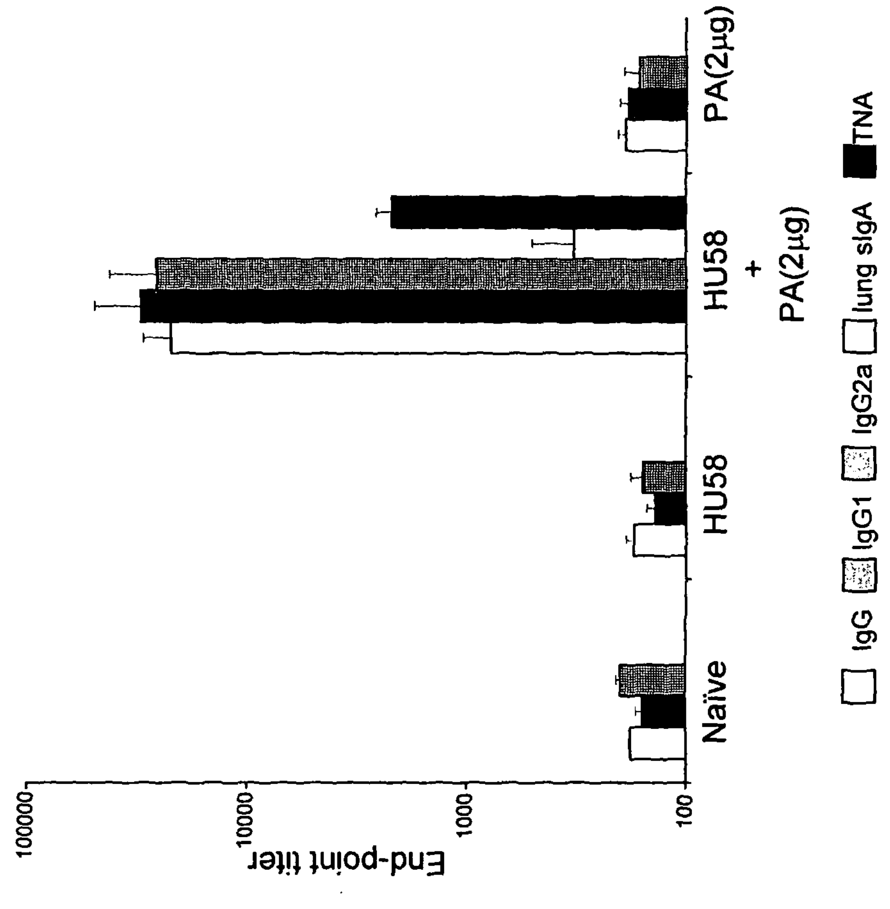

FIG. 9 shows the neutralisation of anthrax toxin. Mice were immunised intra-nasally with HU58 spores pre-adsorbed with PA (2 μg) and serum (IgG, IgG1, IgG2a) and mucosal antibody (sIgA) titres determined. Anthrax neutralising antibodies were determined, in vitro, by the TNA (toxin neutralisation assay). Controls included naïve mice, mice immunised with HU58 spores alone or with PA protein alone. Data are presented as arithmetic means and error bars are standard deviation.

Figure 10:
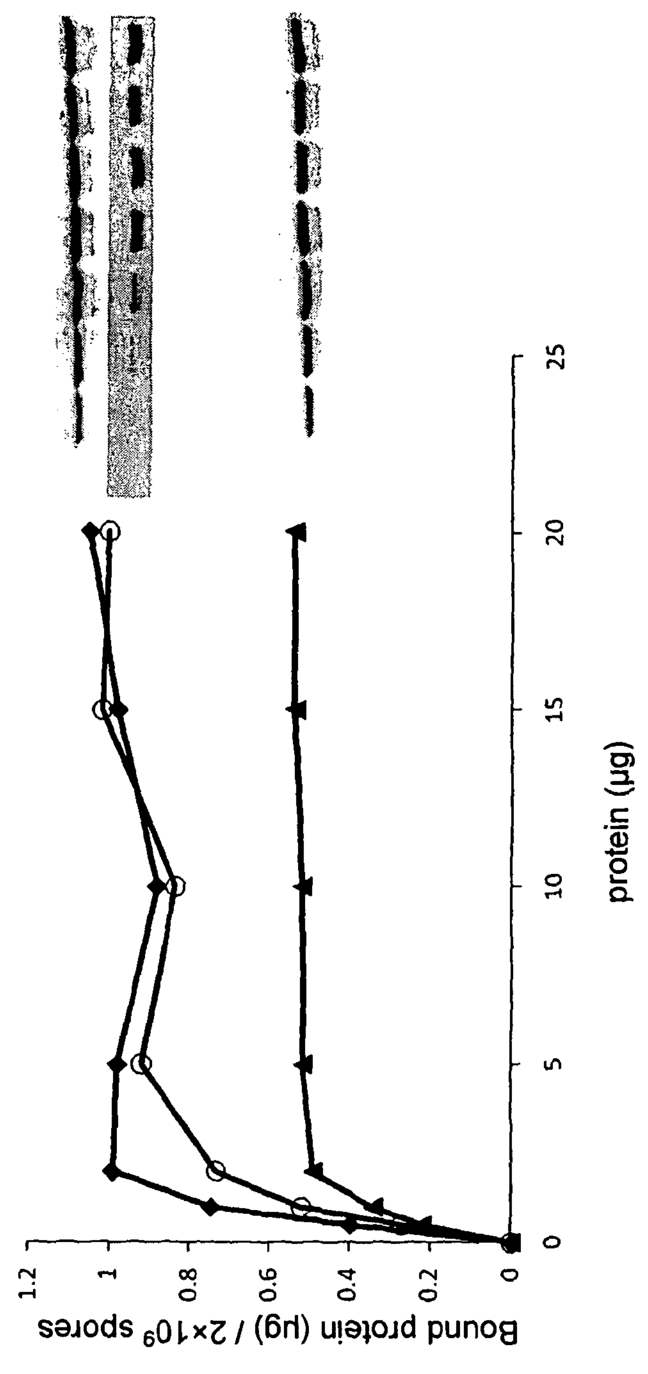
Figure 11B:
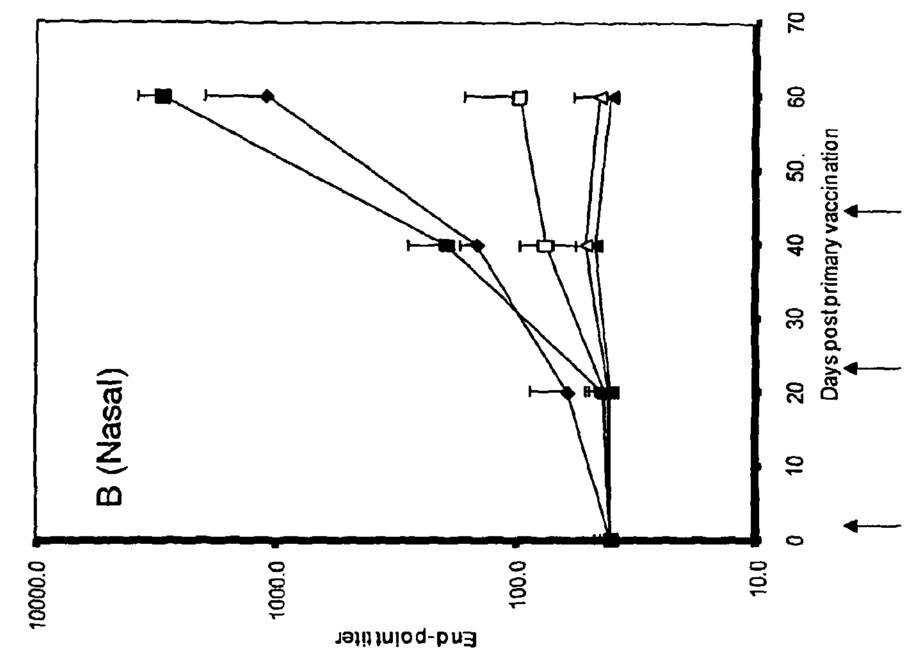
Figure 11A:
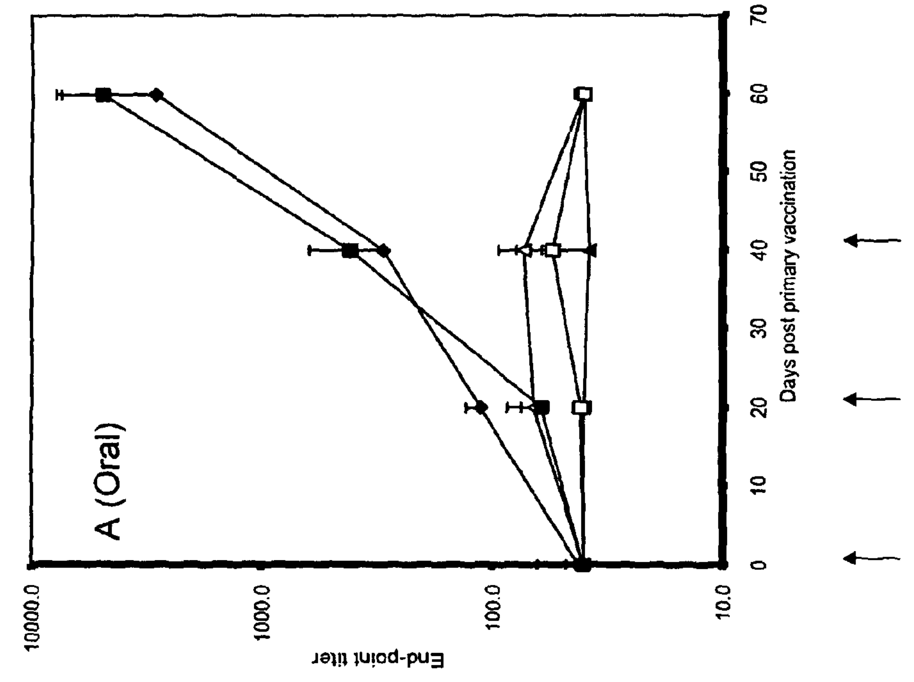
Figure 11C:
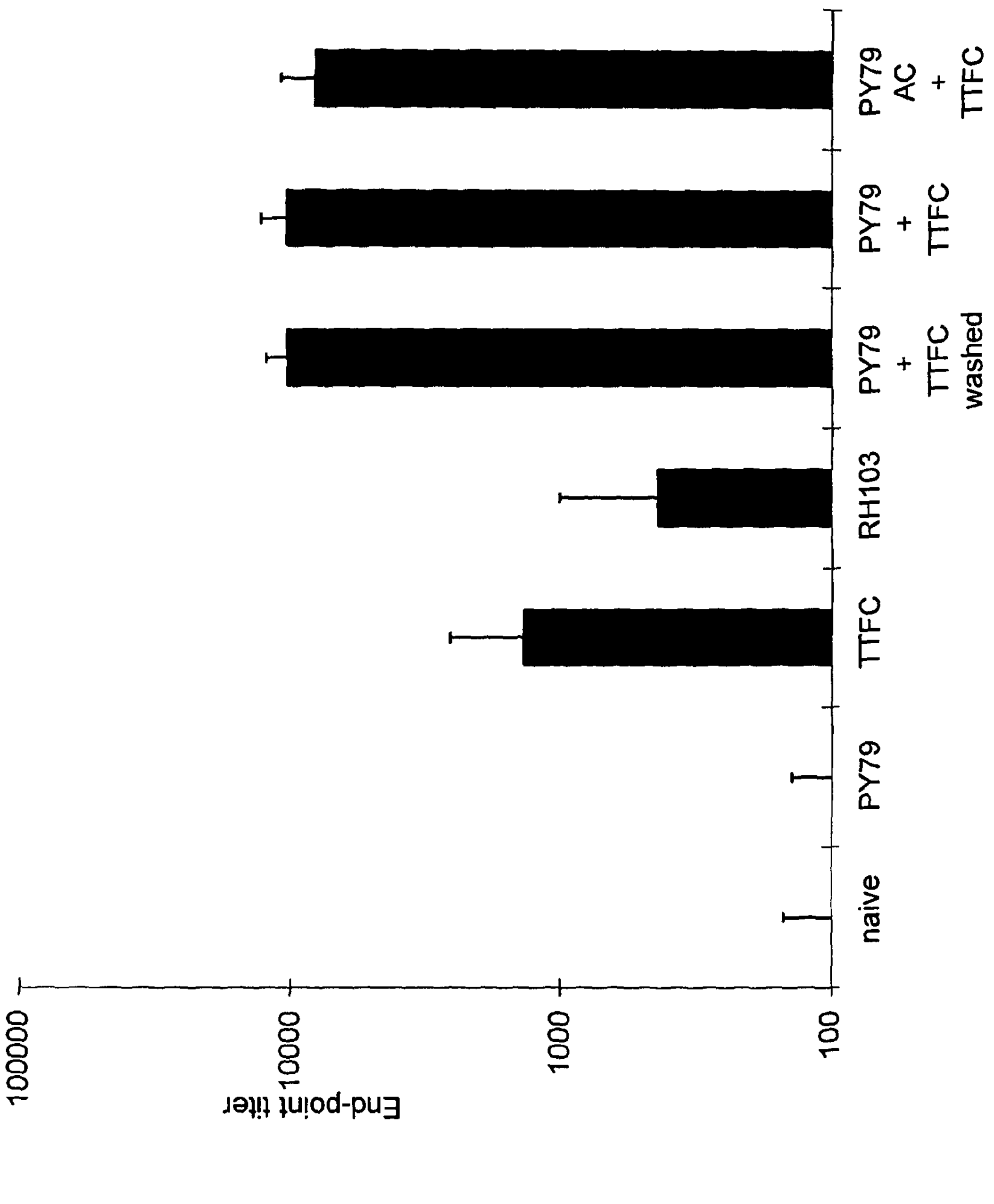
Figure 11D:
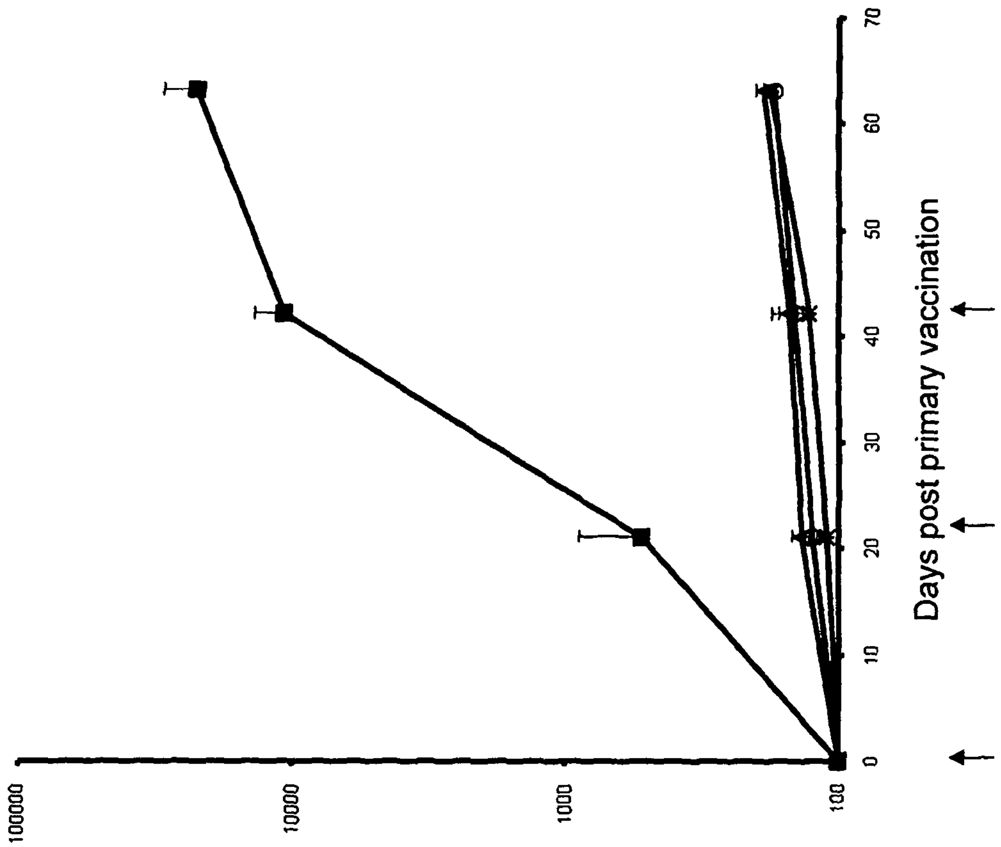

FIG. 10 shows the saturation of binding. Purified recombinant proteins, TTFC (○), GST-$Cpa_{247-370}$ (▲) or PA (♦) were mixed with $2\times10^9$ PY79 spores (TTFC and GST-$Cpa_{247-370}$) or HU58 (PA) and incubated at RT for 1 hour. Spores were centrifuged, washed two times and coat proteins extracted and spore-associated protein detected by Western blotting using appropriate antibodies.

FIG. 11 shows the antigen-specific IgG responses. Antigen-specific IgG was measured in serum from individual mice by ELISA.

Panels A and B: GST-$Cpa_{247-370}$-specific IgG responses after oral (A) or intranasal (B) immunisation. Mice were immunized (↑) with spores of strain HT251 (cotB-GST-$Cpa_{247-370}$; ■), PY79 (non-recombinant; Δ), a pre-adsorbed mixture of PY79 spores and GST-$Cpa_{247-370}$ polypeptide (♦; 3.6 μg/dose for the oral route and 0.15 μg/dose for the nasal), pure GST-$Cpa_{247-370}$ protein (□; 3.6 μg/dose for the oral route and 0.15 μg/dose), and nave un-immunised mice (▲).

Panel C: TTFC-specific IgG responses after nasal administration of spores to mice. Serum was from terminal bleeds of animals immunised as indicated.

Panel D: PA-specific IgG responses after nasal administration (↑) of spores of strain HU58 (○), a pre-adsorbed mixture of HU58 and PA polypeptide (■; 2 μg/dose), pure PA protein (Δ; 2 μg/dose) to mice and a naive group (*) received PBS only.

FIG. 12 shows antigen-specific IgG 1:IgG2a ratios. Serum samples taken from immunisation experiments, as described below, were analysed for the IgG1 and IgG2a subclasses and the relative ratios of IgG1 to IgG2a shown. Panel A: oral immunisations with spores adsorbed with GST-$Cpa_{247-370}$, Panel B: nasal immunisations with spores adsorbed with GST-$Cpa_{247-370}$, Panel C: nasal immunisations with spores adsorbed with PA, Panel D: Antibody titres of IgG1, IgG2a and IgG2b from mice immunised nasally with spores adsorbed with TTFC.

Figure 13B:
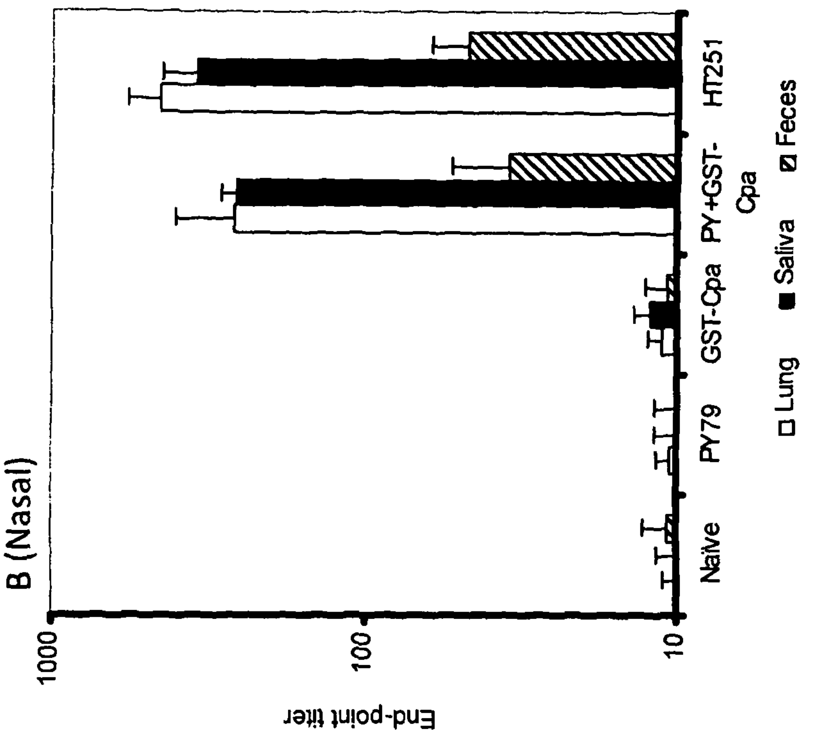
Figure 13A:
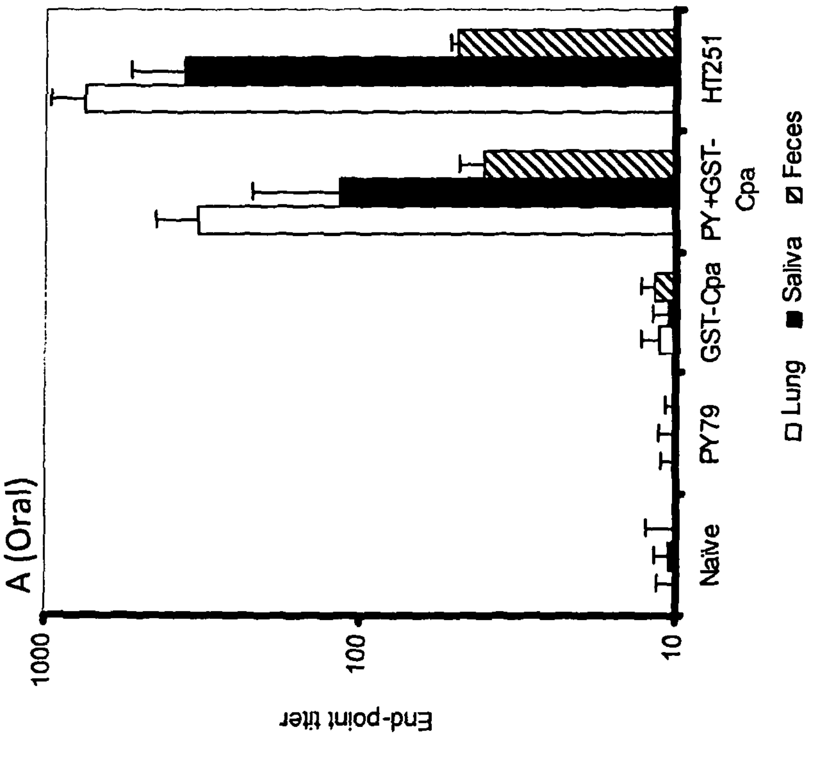
Figure 13C:
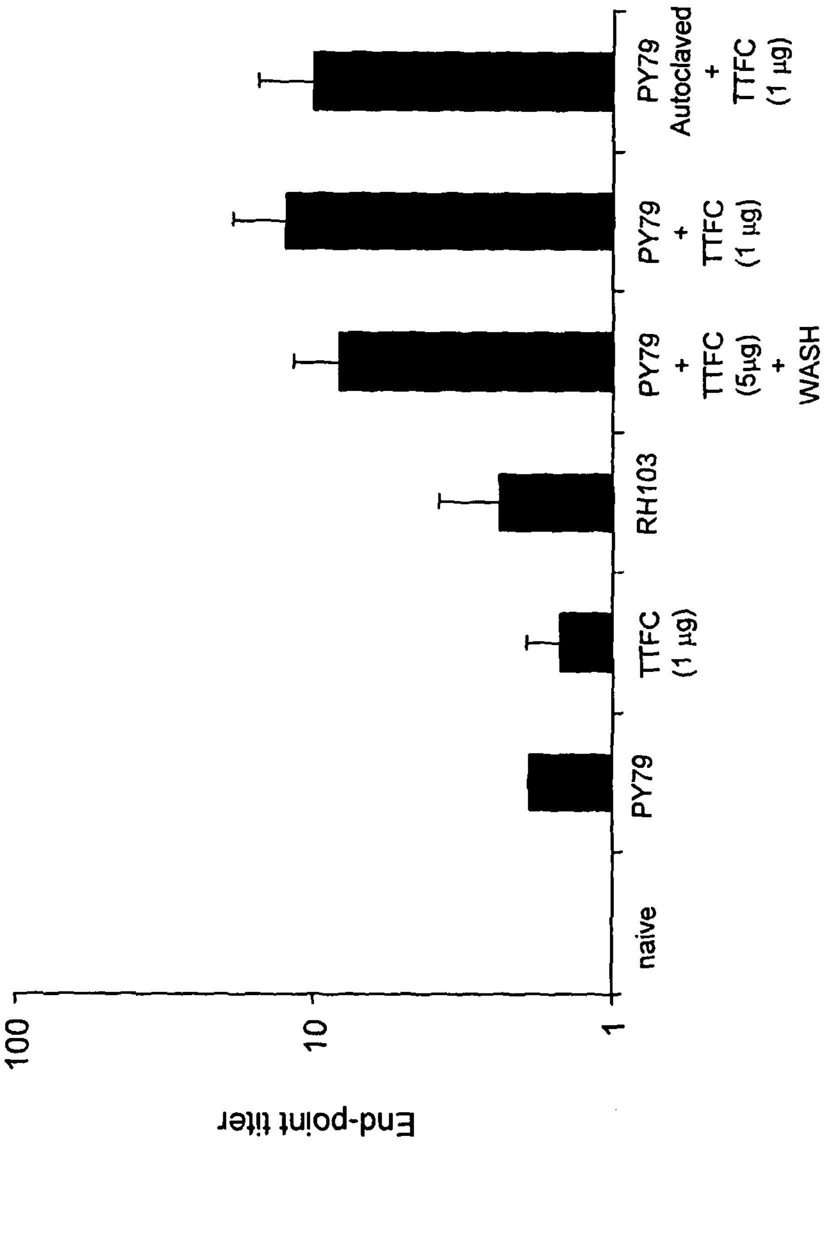

FIG. 13 shows antigen-specific mucosal responses. Antigen-specific sIgA measured in lung washes, saliva and faeces from mice immunised in the immunisations experiments described in the text. Panel A and Panel B shows analysis of GST-$Cpa_{247-370}$-specific IgA taken at day 60. Panel C shows TTFC-specific sIgA obtained in lung washes taken at day 63.

Figure 14A:
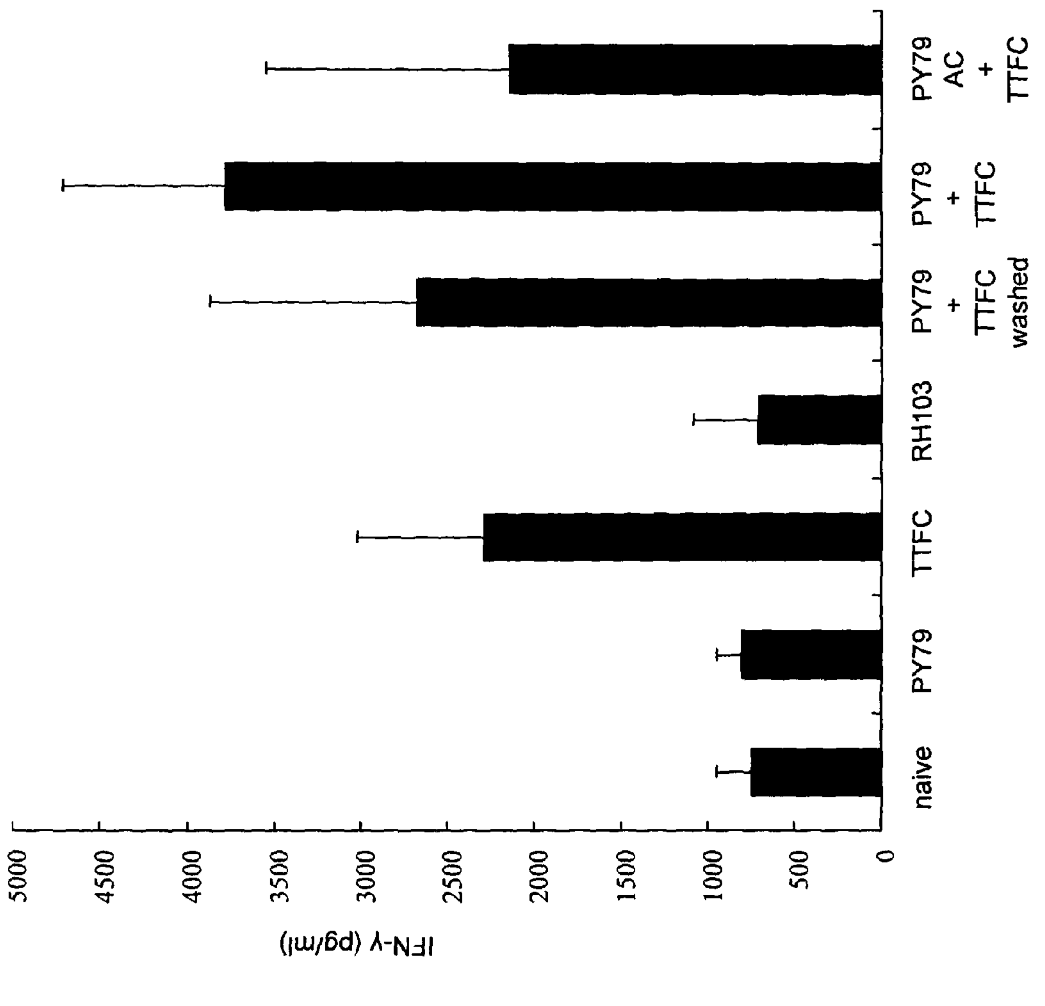
Figure 14B:
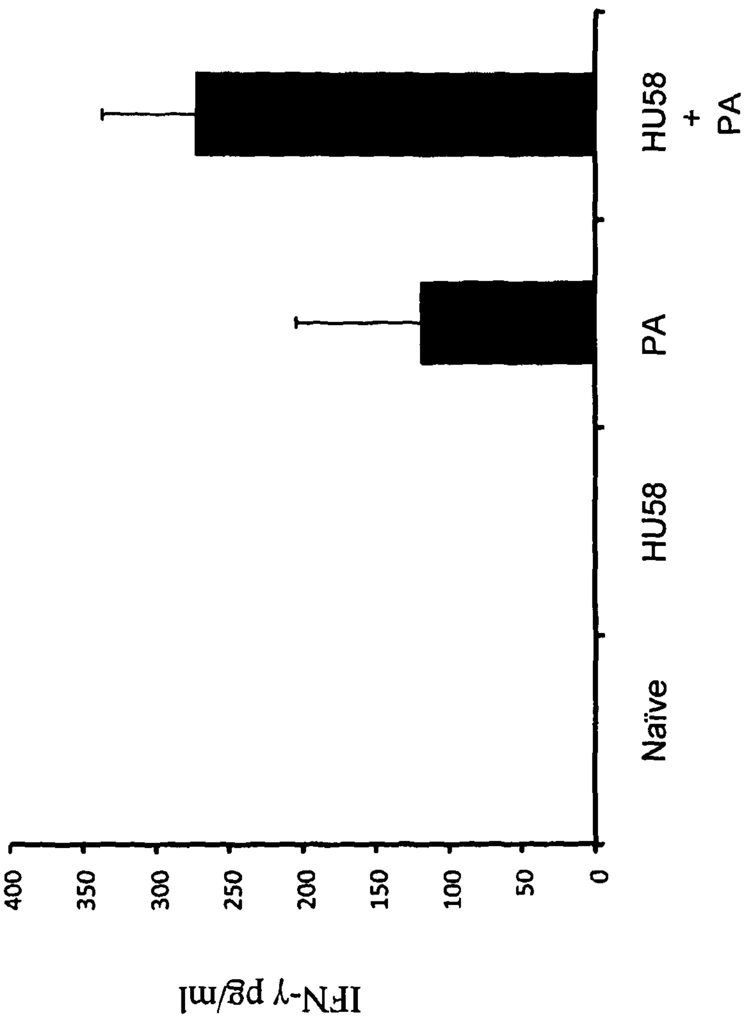

FIG. 14 shows antigen-specific IFN-γ production. IFN-γ responses determined by ELISA from mice immunised with spores as indicated. Splenocytes were extracted from sacrificed mice and re-stimulated with TTFC (Panel A) or PA (Panel B) protein (5 μg/ml). IFN-γ was determined from supernatants after six days incubation.

Figure 15:
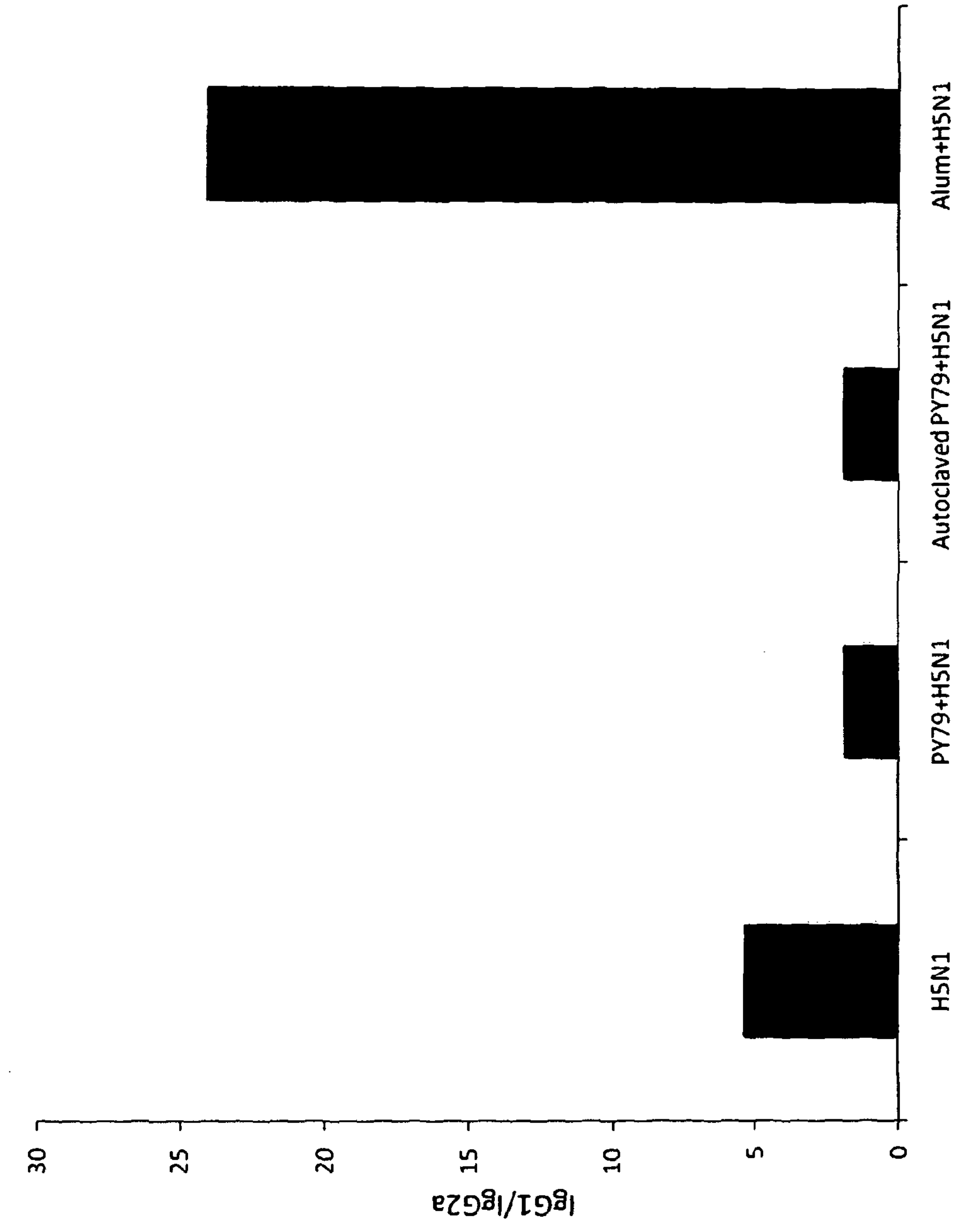

FIG. 15 shows the ratio of IgG1 to IgG2a in mice dosed nasally with a) H5N1 virions, b) PY79 spores coated with H5N1 virions, c) autoclaved PY79 spores coated with H5N1 virions and d) nasally dosed with a suspension of alum and H5N1. In all cases the H5N1 virus preparation (NIBRG-14 from NIBSC) had been formaldehyde-inactivated. Spores are used at $1\times10^7$ spores/binding experiment. The low ratio compared to the high ratio seen with Alum+H5N1 shows clearly that spores confer a Th1 biased immune response. This is beneficial since most adjuvants promote Th2 biased immune responses and thus, high IgG1:IgG2a ratios as shown here with alum. An adjuvant that promotes Th1 biased responses is highly desirable.

Figure 16:
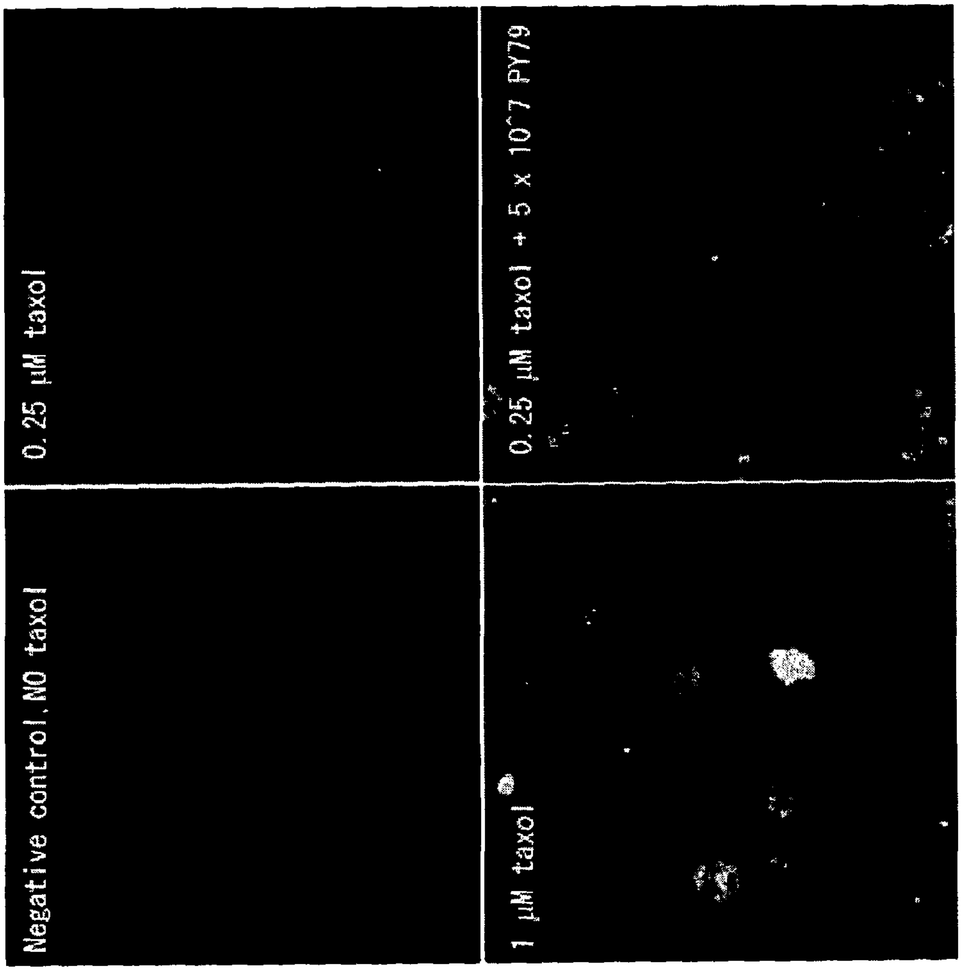

FIG. 16 shows the binding of Paclitaxel Oregon on HCT-116 colorectal cancer cells when being delivered by *B. subtilis* spores. 0 μl, 50 μl and 200 μl of paclitaxel oregon 10 μM was incubated with HCT-116 grown in 2 ml DMEM medium for 4 hours, as negative and positive controls of paclitaxel-oregon at different concentrations used for binding onto HCT-116. The negative control without paclitaxel is in left panel. The binding of paclitaxel at 0.25 uM and 1 uM, respectively, are shown in the upper right and lower left panels. The binding of 0.25 uM paclitaxel oregon adsorbed on $5\times10^7$ spores is shown in the lower right panel.

EXAMPLE 1

Materials and Methods

*Bacillus* Spore preparation

*Bacillus subtilis* strain PY79 and *Bacillus clausii* strain O/C were used to make spores by the exhaustion method on Difco sporulation medium (DSM). Spores were harvested and purified by treating with lysosyme to break residual vegetative cells, washing with NaCL 1M, KCL 1M and sterile water. Then, spores were suspended in sterile water and counted by serial dilution and streaking out on DSM plates before freezing at −20° C. Spores treated in this manner showed better binding capacity than non-treated spores in parallel experiments. The reason for this is considered to be because the lysozyme treatment removes all vegetative cells and the KCl and NaCl treatment removes all proteases, other proteins, peptides, and heavy metal cations that had originated from the culture medium (used to grow spores) and which have non-specifically bound onto the surfaces of the spores. This treatment helps removing molecules causing steric hindrance of hydrophobic binding sites on the outer surfaces of spores, thereby increasing exposure of the binding sites for interaction with antigens.

Adsorption and Desorption Experiments

In this study, the inventors designed the experiment to consider the effects of pH, salt concentration, the time of maximum adsorption, the strength of binding and the adsorption characteristics of autoclaved compared to non-autoclaved spores. The binding buffers were Phosphate Buffer Saline (PBS) prepared at different pH (4, 7, 10) and concentration of phosphate buffer (0.001M, 0.01M, 0.1M) containing different concentrations of NaCl depending on the purpose of each experiment. The amount of $2\times10^9$ spores of strain PY79 and O/C (autoclaved and non-autoclaved spores) were washed two times with sterile water before use and suspended in 200 μl of binding buffer; leave 15 minutes to charge spores. Then, 10 μl of alkaline phosphatase (AP) (0.4 μg/μl) was added to $2\times10^9$ spores of PY79 or O/C suspensions, gently and continuously shaking in 45 minutes at RT. After incubation for adsorption, the pellets of spores were collected by centrifuging and washed 3 to 5 times with binding buffer or elution buffer.

Alkaline Phosphatase Activity Assay

The phosphates assay used in this study to detect the appearance of AP on spores is well known to those skilled in the art. In particular, the p-Nitrophenyl Phosphate (pNPP) substrate was prepared in a solution with a concentration 1 mg/ml in diethanolamine buffer (diethanolamine/HCl 100 mM, $MgCl_2$ 0.5 mM, pH 9.8). See The Protein Protocol Handbook, John M. Walker. The pellet of spores was suspended with 100 μl of diethanolamine buffer containing pNPP (1 mg/ml) substrate and incubated 45 minutes at room temperature. In this assay, the p-Nitrophenol and phosphate group were produced with the catalysis of AP, and p-Nitrophenol is a coloured compound that absorbs light with a wavelength of 405 nm. After developing the colour, the supernatant was collected by centrifuging and measured OD at 405 nm. In order to quantify the amounts of adsorbed AP on spores based on enzymatic activity, AP was prepared in serial dilutions and the activity determined in parallel with the test of absorbed AP on spores to build the standard curve. The amount of AP on spores was calculated by comparing the enzyme activity between standard AP solutions and adsorbed AP on the spore based on the standard curve.

The method to quantify adsorbed AP on spores was confirmed and compared with the Western blot. After binding AP to spores, the spore coat proteins were extracted by use of an SDS-dithiothreitol extraction buffer as described elsewhere. The extracted proteins were run on SDS-PAGE and a Western blot made using an anti-AP antibody.

Results

Adsorption of Alkaline Phosphatase on *Bacillus* Spores

In this experiment, the inventors examine the influence of pH on adsorption of AP to *Bacillus* spores. The binding and washing conditions were performed in the same buffer at different pH (pH4, pH7 and pH10). The results showed that the adsorption of AP on spores occurred highly at p1-14 and was strongly reduced at pH7 and pH 10, autoclaved spores also were pH dependent, with highest adsorption at pH4. See FIG. 1.

The influence of ionic strength on AP absorption on *Bacillus* spores was studied by designing experiments with binding buffers (PBS pH4, 0.01M) containing different concentrations of NaCl from 0 to 1M. See FIG. 2. The results showed that the adsorption of alkaline phosphatase on O/C spores occurred highly at low concentration of NaCl and strongly decreased with high concentrations of NaCl.

However, the adsorption of AP on PY79 occurs highly at low concentrations and at high concentrations of NaCl (0.5M, 1M). This point could be explained by the increasing hydrophobicity of PY79 spores, and this point was not observed on O/C spores.

In order to understand more about the adsorption, the experiments of adsorption were performed in a different phosphate buffer (0.001M, 0.01M, 0.1M), the results showed that the adsorption increased with the concentration of phosphate buffer (see FIG. 4).

Desorption of Alkaline Phosphatase from *Bacillus* Spores

For more evidences to illustrate the mechanisms of AP adsorption on spores, the experiments were conducted to consider desorption of AP from spores. The binding was performed in PBS and washing steps were done with PBS containing 1M NaCl or 1% Triton-X. Importantly, AP activity was considered in different elution buffers, the results indicating that the activity of AP was the same (data not shown). The data showed that high salt concentrations (1M NaCl) could dissociate small amounts of the AP from spores while a large amount of AP was eluted by 1% Triton-X. Interestingly, the mixture of 1M NaCl and 1% Triton-X could dissociate nearly all the AP from the spores. See FIG. 3.

Discussion

The Isoelectric Point (pI) of a protein is the pH at which the protein carries no net electrical charge. At a pH below the pI, proteins carry a net positive charge and above pI protein become negatively charged. Moreover, the spore coat and exosporium of *Bacillus* endospores are comprised of complex layers of protein. Therefore spores essentially carry the electrical properties of protein (P. Maarten Bieshaeuvel et al., 2004; Christopher J. Daughney et al., 2000). *Bacillus* spores are featured by the Zero Point of Charge (ZPC). They are negatively charged at a pH above the ZPC because of the deprotonation of the functional groups such as carboxylate, phosphate and amino groups. They become positively charged at a pH below the ZPC because of protonation of major groups on the spore surface. (Lee M. He and Bradley M. Tebo, 1997). The ZPC of O/C and PY79 spores were determined as nearly 2 (ZPC≈2) and the pI of AP is 4.5. Consequently, spores that were negatively charged can adsorb positively charged AP at pH4 based on electrical interaction. However, there is some AP adsorbed on spores at pH7 and pH10. This discrepancy suggests the minor participation of other mechanisms, such as hydrophobic interaction in protein adsorption.

Hydrophobic interactions and pH are considered to be inversely related. As the pH increases, the hydrophobic interactions decrease. (Deirdre A. Small et al, 1986). This point is explained by the charge-masking effect, for example, the carboxyl groups ($pK_2$: 4-5) are uncharged at pH4 because they become protonated (COOH) at pH below 4, therefore hydrophobicity of spores increases (Nathan Yee et al., 1999). The present data indicates that most of the protein is adsorbed at pH 4 and the level of adsorption strongly decreased at pH7 and pH10. Therefore, the adsorption of protein on spores is due to both ionic interactions and hydrophobic interactions.

The data of adsorption at different concentrations of NaCl showed that AP adsorbed to O/C spores increased with decreased NaCl concentration, while AP adsorbed to PY79 highly at both low and high concentration of NaCl, The adsorption of AP on spores increased with low concentration of NaCl indicating that the ionic interaction was dominant and could be explained by increasing the proportion of free migrating AP in the NaCl containing binding buffer (Z. Zhang et al., 2003). In addition, hydrophobic interactions plays a role in PY79 adsorption. These results were matched with hydrophobicity data that O/C spores were hydrophilic and PY79 were highly hydrophobic. Accordingly, depending on the spores being used, the hydrophobicity of the binding solution may have an effect on adsorption of the therapeutic agent.

It is clear that the level of hydrophobic interactions can be increased by using a variety of different salt concentrations depending on the spore/therapeutic agent combination. In order to determine the optimum salt concentration different salt concentrations should be tested as outlined above.

EXAMPLE 2

Materials and Methods

Strains

*B. subtilis* strain PY79, is a standard prototrophic laboratory strain and isogenic to the 168 type strain (Youngman et al., 1984). HU58 is a non-domesticated isolate of *B. subtilis* (Tam et al., 2006). HT251 (amyE::cotB-GST-$Cpa_{247-370}$) is isogenic to strain PY79 and carries a recombinant gene on its genome that expresses a modified spore coat protein, CotB, that has been fused to GST-$Cpa_{247-370}$ (Hoang et al., 2008). RH103 (amyE::cotB-tetC) expresses the immunogen, TTFC (tetanus toxin fragment C) from *Clostridium tetani* on the spore surface as a chimera fused to the CotB protein (Isticato et al., 2001).

Preparation of Spores

Spores used in all experiments were prepared by growth and sporulation in Difco Sporulation Medium (DSM) as described elsewhere (Nicholson et al., 1990). Each batch of spores was heat-treated (68° C., 45 minutes) to ensure killing of all vegetative cells. Spores were suspended in sterile PBS (pH 7.4) and stored in aliquots ($1\times10^{11}$ spores/ml) at −70° C. until use. Spore counts were determined by (i) direct counting using a haemocytometer and phase-contrast microscopy and, (ii) by serial dilution and plate-counting. Extraction and analysis of spore coat proteins using SDS-PAGE was as described (Nicholson et al., 1990).

Zeta Potential Measurements

Zeta potentials of the two spore isolates were measured at 24° C. with a 3000HS Malvern Zeta-sizer (Malvern Instruments Ltd, UK). Aliquots of 30 µl of spores suspended in Milli-Q water at a density of $5\times10^9$ spores $ml^{-1}$ were added to 3 ml solutions of defined pH and ionic strength, as described below. The pH was adjusted using HCl or NaOH. The mean of two separate measurements from the same sample was determined. The zeta potential was calculated from the electrophoretic mobility using the Smoluchowski equation (Sze et al., 2003).

Spore Adhesion to Hydrocarbon (SATH) Assay

The surface hydrophobicity of the two spore isolates was determined using the spore adhesion to hydrocarbon (SATH) assay using n-hexadecane as hydrocarbon (Seale et al., 2008). Purified spores were washed in either Milli-Q water or 1 M NaCl in Milli-Q water by centrifugation at 16,000 g for 10 min and resuspended in 0.1 M NaCl at a density of $1\times10^8$ spores $ml^{-1}$. Spore suspensions (2 ml) were added to 1 ml n-hexadecane (Aldrich) and vortexed for 1 min, incubated at 37° C. for 10 min, and vortexed again for 30 seconds. The absorbance of the aqueous phase was measured at 600 nm. The mean of two measurements was determined. The percent hydrophobicity (% H) was determined from the absorbance of the original spore suspension ($A_i$) and the absorbance of the aqueous phase after incubation with hexadecane ($A_f$) according to the following equation: $\% H=[(A_i-A_f)/A_i]\times100$.

Recombinant Proteins

Proteins were expressed from recombinant plasmids in the *E. coli* strain BL21. With the exception of GST-$Cpa_{247-370}$, the expressed protein carried a poly-histidine tag at its 3'-end and following expression was purified using an AKTA chromatography system (Pharmacia).

(i) TTFC: pET-28b-TTFC expressed *C. tetani* TTFC as a 52.6 kDa polypeptide and has been described elsewhere (Duc et al., 2003).

(ii) PA: pET-28b-PA expressed the 83.5 kDa protective antigen (PA) from *Bacillus anthracis*. As described elsewhere, in this cassette the secretory signal sequence permitting membrane secretion was deleted (Duc et al., 2007).

(iii) GST-$Cpa_{247-370}$: The 41 kDa hybrid protein of Sj26GST fused to the carboxy-terminal domain of *Clostridium perfringens* alpha toxin ($Cpa_{247-370}$ has been described elsewhere (Williamson et al., 1993) and was purified using a GST-binding column.

(iv) GST: pET-28b-GST expressed the 26.3 kDa glutathione S-transferase (Sj26GST) from *Shistosomas japonica* (Walker et al., 1993). Henceforth Sj26GST is referred to as GST. The sj26GST gene was PCR-amplified and cloned from the vector pGEX3X13 (Pharmacia).

Antibodies

Polyclonal antibodies were raised in mice immunised by the intra-peritoneal (i.p.) route with 2 μg of purified protein on days 1, 14 and 28. Dilutions used were 1:1000 for anti-PA and 1:2000 for anti-TTFC and anti-GST-$Cpa_{247-70}$.

Binding Assays

Unless indicated otherwise the general method for adsorbing proteins to spores was as follows. Suspensions containing $2\times10^9$ spores were centrifuged and resuspended in 0.2 ml of PBS at pH 4, pH 7 or pH 10. Unless indicated otherwise all reactions were performed in PBS at 0.15M. Purified recombinant proteins were added to the spore suspension and the binding solution incubated at room temperature (RT). Spores were centrifuged (1 minute, RT) and the pellet washed two-times with PBS buffer of the same pH as that used in the binding solution. The washed pellet was resuspended in 100 μl of spore coat extraction buffer (Nicholson et al., 1990), incubated at 68° C. for 1 h to solubilise spore coat proteins and one tenth loaded onto a 12% SDS-PAGE gel.

Animals

Animals used in this work were pathogen-free, Balb/c mice (Harlan UK) for antibody production, and for analysis of immune responses with PA or GST-$Cpa_{247-370}$. For TTFC immunity studies C57BL/6 mice (Charles River) were used. In all cases females, aged 6-8 weeks were used. Animals were housed in the Royal Holloway, University of London's animal house and work was performed under the Home Office project licence PPL 70/6126.

Immunisations

Mice were dosed by the intra-nasal route (light anesthesia, 20 μl using a pipette tip) or intra-gastrically (oral; 0.2 ml by gavage). A naïve group of un-immunised animals was included in all experiments.

(i) TTFC studies: Groups of mice (3-10 as specified) were immunised nasally with, i) purified TTFC protein, ii) a pre-adsorbed (PBS, pH 4) mixture of PY79 spores ($2\times10^9$ cfu) and TTFC protein (1 μg), or iii) a pre-adsorbed (PBS, pH 4) mixture of PY79 spores ($2\times10^9$ cfu) and TTFC protein (5 μg) that had been washed two times with PBS buffer (pH 4). A further group consisted of autoclaved PY79 spores ($2\times10^9$ cfu; 15 p.s.i., 30 minutes) that had been pre-adsorbed (PBS, pH 4) with TTFC (1 μg). Control groups included naïve (PBS, pH 4) and a group receiving PY79 ($2\times10^9$ cfu) spores by the intra-nasal route. The dosing regime consisted of immunisations on days 1, 15, 29 and 43. One additional group of mice was given $2\times10^{10}$ cfu RH103 spores (in PBS, pH 7.4) orally on days 1, 2, 3, 22, 23, 24, 43, 44 and 45 as a positive control. Mice were challenged with *C. tetani* tetanus toxin on day 64.

(ii) GST-$Cpa_{247-370}$ studies: Groups of six mice were immunised by either the intra-nasal or oral routes on days 1, 21 and 42 after which the challenge was performed on day 63. For oral immunisations groups included animals receiving PY79 spores ($5\times10^{10}$ cfu), GST-$Cpa_{247-370}$ protein (3.6 μg) and a further group receiving a mixture of PY79 spores ($5\times10^{10}$ cfu) that had been pre-adsorbed (80 minutes RT; PBS pH 7.4) with 3.6 μg of GST-$Cpa_{247-370}$. A positive control consisted of $5\times10^{10}$ cfu spores of HT251 (amyE::cotB-GST-$Cpa_{247-370}$). For intra-nasal dosing one group received PY79 spores ($2\times10^9$ cfu), another group GST-$Cpa_{247-370}$ protein (0.15 μg) and a further group a pre-adsorbed (80 minutes RT; PBS pH 7.4) mixture of PY79 spores ($2\times10^9$ cfu) and GST-$Cpa_{247-370}$ protein (0.15 μg).

(iii) PA studies: Groups of six mice were dosed intra-nasally on days 1, 22 and 43. Groups received HU58 spores ($2\times10^9$ cfu) or the same quantity of HU58 spores that had been adsorbed with 2 μg of PA (protective antigen of *B. anthracis*) protein for 1 h in PBS (pH 4).

Humoral Responses

For analysis of anti-GST-$Cpa_{247-370}$ responses serum, saliva and faecal pellets were taken on days −1, 20, 40 and 60. For PA-specific responses, serum samples were taken on days −1, 21, 42 and 63 and for TTFC-responses terminal bleeds were used for IgG analysis. Lung washes for extraction of sIgA was done on lungs taken from sacrificed animals performed as described (Uyen et al., 2007). Determination of antibody titres by ELISA was as described elsewhere (Duc et al., 2003; Hoang et al., 2008).

IFN-γ ELISA

Spleen cells ($5\times10^5$) taken from mice were dosed with immunogen (protein, spores or protein and spores), seeded in 96-well cell culture plates in complete medium, were stimulated with 5 μg/ml of either TTFC or PA protein, 1 μg/ml ConA was used as a positive control or with medium only and cells were incubated at 37° C. in 5% $CO_2$. Supernatants were harvested from cultures after six days and analysed for IFN-γ as described (Hoang et al., 2008). IFN-γ (BD Biosciences) was used as a standard.

Toxin Neutralising assays (TNA)

Measurement of anthrax toxin neutralising activity was done as described previously using a RAW264.7 cell-line (Duc et al., 2008).

Toxin Challenges

Challenge of immunised mice with *C. tetani* tetanus toxin or *C. perfringens* alpha toxin were performed as described previously (Duc et al., 2003; Hoang et al., 2008). Note that challenge experiments were conducted in experiments independent from studies in which immune responses were evaluated.

Statistics

The Student's t test was used to compare between groups. A P value of >0.05 was considered non-significant.

Results

Oral Vaccination of Mice with Spores Preadsorbed with an Immunogen Protects Mice Against Challenge with *C. perfringens* Alpha Toxin In a previous study, a recombinant *B. subtilis* strain, HT251, was engineered to express GST-$Cpa_{247-370}$ on the spore surface fused to the outer spore coat protein CotB (Hoang et al., 2008). $Cpa_{247-370}$ is the C-terminal fragment of *C. perfringens* alpha toxin (Cpa) and when fused to GST has been shown to confer protective immunity (Williams et al., 1993). Mice dosed orally or nasally with HT251 spores were protected against a 12 $LD_{50}$ challenge dose of alpha toxin. Using the same dosing regime as with recombinant HT251 spores, mice were dosed with a mixture of GST-$Cpa_{247-370}$ protein and non-recombinant PY79 spores. For the oral route, for each dose, 3.6 μg of GST-$Cpa_{247-370}$ was mixed with PBS buffer (pH 7.4) corresponding to the amount of recombinant GST-$Cpa_{247-370}$ expressed in one single dose of HT251 spores. For the nasal route 0.15 μg was used. The inventors analysis of GST-$Cpa_{247-370}$-specific IgG titres following oral and intra-nasal dosing revealed that the levels and kinetics of antibody responses were indistinguishable from recombinant HT251 spores. By contrast, PY79 spores and protein alone produced no significant levels (P>0.05) of GST-$Cpa_{247-370}$-specific responses. The inventors evaluated the ability of mice immunised with spore-immunogen mixtures to survive challenge with alpha toxin (Table 1). Protection was obtained in nasally dosed mice although to lower doses of toxin (6 $LD_{50}$) while for oral dosing one mouse was able to survive the same dose of toxin (6 $LD_{50}$). Since neither spores nor protein alone could induce antibody responses the most straightforward explanation is that spores associate with the administered antigen facilitating their interaction and uptake by immune cells.

Adsorption of Proteins to Spores

To determine whether a protein immunogen could bind to spores the inventors designed an adsorption experiment mixing the GST-$Cpa_{247-370}$ protein (mwt., 40.4 kDa; pI, 5.7) with PY79 spores and then analysing samples of spore coat protein extract and supernatants for the presence of GST-$Cpa_{247-370}$ by immunoblotting (FIG. 5A). The data showed that at pH 4 and pH 7, GST-$Cpa_{247-370}$ was efficiently adsorbed onto the spore coat but with low levels of binding at pH 10. The inventors calculated by immuno-quantification that $2.6\times10^4$ pg of protein had adsorbed per spore (~$3.7\times10^3$ molecules/spore).

The inventors extended this study by determining whether other protein antigens could be adsorbed onto the spore surface. Using tetanus toxin fragment C (TTFC; mwt., 52.6 kDa; pI, 6.34)) of *Clostridium tetani* and the protective antigen (PA; mwt., 83.5; pI, 5.87) of *Bacillus anthracis* both antigens were found to bind efficiently to spores (FIG. 5A). In both cases though, binding was only detected at pH 4 with $4.9\times10^4$ μg of TTFC bound/spore ($5.4\times10^3$ molecules/spore) and $4.6\times10^4$ pg of PA/spore ($3.2\times10^3$ molecules/spore). The inventors measured the saturation of binding by adsorbing increasing amounts of protein to a suspension of $2\times10^9$ PY79 spores and found that the maximum amount of TTFC or GST-$Cpa_{247-370}$ that could adsorb to spores was ~1.0 μg of TTFC or ~0.5 μg GST-$Cpa_{247-370}$/$2\times10^9$ spores (see FIG. 10).

Since GST-$Cpa_{247-370}$ was a chimera of GST and Cpa the inventors wondered whether the reduced but still measurable binding observed at pH 7 and pH 10 was due to one of the component polypeptides. Cpa was unstable without fusion to GST so binding of GST alone was examined (FIG. 5A). GST was found to bind at all three pH values and while we cannot be certain it is possible that GST confers upon the GST-$Cpa_{247-370}$ polypeptide the ability to bind at all three pH conditions. Surprisingly, each of the three proteins studied here could adsorb to autoclaved PY79 spores as efficiently as 'live' spores (FIG. 5B shows binding of TTFC). Since spores adsorbed with GST-$Cpa_{247-370}$ were able to generate some immune response following oral administration the inventors investigated whether the spore conferred protection to simulated gastric juices containing pepsin as described elsewhere (Barbosa et al., 2005). Under these conditions the inventors failed to detect any protection conferred by the spore to the adsorbed protein that was degraded (data not shown). Since the outermost layer of the spore coat of *B. subtilis* is comprised exclusively of five coat proteins, CotA, CotB, CotC, CotG and CotF the inventors examined adsorption of proteins onto isogenic null mutants lacking each of the Cot genes. In each case the inventors were able to show that protein adsorption was less than in wild type PY79 spores but never abolished (data not shown). It is inferred then that adsorption is mainly multivalent and non-specific.

The stability of binding was examined by measuring the dissociation of bound immunogen (TTFC) from adsorbed spores (FIG. 5C). The results showed that TTFC bound to spores at pH 4 was stable for at least 90 min with no significant dissociation. When suspended in buffers of higher pH only a small amount of protein was detectable in the supernatant demonstrating that protein adsorption to spores was stable. All three recombinant proteins were shown to bind rapidly to spores and maximum levels of binding being achieved in approximately 10 minutes (FIG. 6).

The surface hydrophobicity of PY79 spores was characterized by the spore adhesion to hydrocarbon (SATH) assay (Seale et al., 2008) and electro kinetic properties were characterized by zeta potential measurements (Ahimou et al., 2001). The zeta potentials of spores was determined between pH 1 and 12 in water (FIG. 7) with negative zeta potentials presented over the entire pH range. Remarkably, the zeta potential presented a significant peak broadening at pH 1, indicating that this pH is close to the isoelectric point. In complementary experiments, zeta potentials were measured at pHs 3, 5 and 7 for spores suspended in the presence of either 1 M NaCl or 5 mM $CaCl_2$. The zeta potentials were higher than those measured in water, yet remained negative (data not shown). The fact that zeta potentials become less negative in the presence of $Na^+$ or $Ca^{2+}$ ions is due to the cation-specific screening effect exerted on spore negative charges. Using the SATH assay PY79 spores presented an almost constant hydrophobicity, close to 95%, over the pH range of 3 to 8 (FIG. 7).

Ionic and Hydrophobic Interactions are Important for Protein Adsorption

That protein adsorption was greatest at pH 4 suggested that ionic interactions must play a major role in binding. Proteins with a net positive charge would be expected to efficiently bind to PY79 spores exhibiting a net negative charge. However, the inventors found that spores adsorbed with TTFC that had been washed with 1M NaCl only removed approximately 30% of the bound immunogen demonstrating that binding could not be exclusively ionic in nature (FIG. 8A). Washing with Triton X-100 though, failed to release the adsorbed protein but washing with a combination of Triton X-100 and NaCl removed approximately 70% of the bound protein demonstrating hydrophobic interactions (FIG. 8A).

The inventors also measured adsorption of TTFC in PBS buffers (each at pH 4) containing different concentrations of NaCl (FIG. 8B). At very low salt concentrations binding was strong and sharply declined as the concentration increased to about 1 M. At NaCl concentrations above 1 M binding of TTFC steadily increased to its highest levels at 4M NaCl. The binding studies shown in FIG. 1 were made in PBS buffer at 0.15 M (pH 4) enabling high levels of binding where charge plays the dominant role in adsorption. The increasing ability of protein to bind at higher salt concentrations indicates the importance of hydrophobic interactions for this particular spore/therapeutic agent combination (Shields et al., 1983).

Inactive Spores Can Be Used as a Vaccine Delivery Vehicle.

TTFC is the protective antigen used in evaluations of vaccines against tetanus (Fairweather et al., 1987). It has been expressed on the spore coat as a chimera fused to the spore coat protein CotB where oral delivery of recombinant spores has been shown to protect against challenge with tetanus toxin (Duc et al., 2003). The inventors constructed a series of experiments to determine the efficiency of PY79 spores to deliver TTFC intra-nasally using a challenge experiment at the end of the dosing regime (Table 1). One group of mice was dosed with spores that had been mixed with an excess of TTFC protein (5 μg) at pH 4 and then washed with PBS (pH 4) to remove any unbound protein. The amount of TTFC that could bind under these conditions was calculated as approximately 1 μg/dose.

Mice dosed with these spores were protected against a tetanus toxin challenge dose of 50 $LD_{50.}$ Other groups of mice examined were animals dosed with PY79 spores that had been mixed with 1 μg of TTFC without washing and which also showed protection against a challenge dose of 50 $LD_{50}$. Mice dosed with the same quantity of TTFC protein, but without spores, failed to be protected though. One further immunisation group was animals dosed with autoclaved PY79 spores that had been adsorbed with TTFC protein (1 μg). These animals showed the same level of protection to challenge with tetanus toxin (50 $LD_{50}$). As a control the inventors also immunised mice by the intra-gastric route with recombinant RH103 spores that expressed TTFC on the spore surface. Using $2\times10^{10}$ spores for each immunisation approximately 2 μg of TTFC would be delivered per dose and the inventors were able to achieve protection to a 20 $LD_{50}$ challenge dose in agreement with previous work (Duc et al., 2003). These experiments demonstrate firstly, that spores preadsorbed with an antigen can be delivered by a mucosal route and confer protection against a systemic pathogen. Second, that inactive or killed, spores are as efficacious as live spores.

Vaccination Against Anthrax

Recombinant *B. subtilis* spores that express the protective antigen (PA) of *B. anthracis* have been shown to protect mice against challenge with anthrax toxin when administered by a parenteral route (Duc et al., 2007). The production of toxin neutralising antibodies was shown to be dependant upon display of PA (or fragments of PA) on the spore surface or secretion from the germinating spore. In light of the inventors' studies with TTFC and GST-$Cpa_{247-370}$ they determined whether PA, adsorbed to spores, could be used to vaccinate mice against anthrax. In the first instance, the inventors measured toxin neutralising antibodies (TNA) as an indicator since studies have shown that the level of neutralising antibodies correlates well with protection (Duc et al., 2007; Flick-Smith et al., 2002; Flick-Smith et al., 2002). To determine whether the binding phenomena was specific to the laboratory PY79 strain the inventors used a non-domesticated strain of *B. subtilis* referred to as HU58 for binding (Tam et al., 2006). The inventors first confirmed binding of PA to HU58 spores at pH 4, with approximately $9.34\times10^{-4}$ pg of PA bound per spore-almost double that obtained with PY79 spores. Mice dosed nasally with HU58 spores adsorbed with PA generated high levels of PA-specific IgG and sIgA compared to groups dosed with HU58 spores or PA alone (FIG. 9). Neutralising antibodies (a titre of 2,000) were only obtained in mice dosed with spores adsorbed with PA (FIG. 9) and were greater than the amount (1,000) that have been shown to protect mice against an intra-peritoneal challenge of $>10^3$ MLD (2,000 $LD_{50}$) of *B. anthracis* STI spores (Duc et al., 2007; Flick-Smith et al., 2002).

Figure 12A:
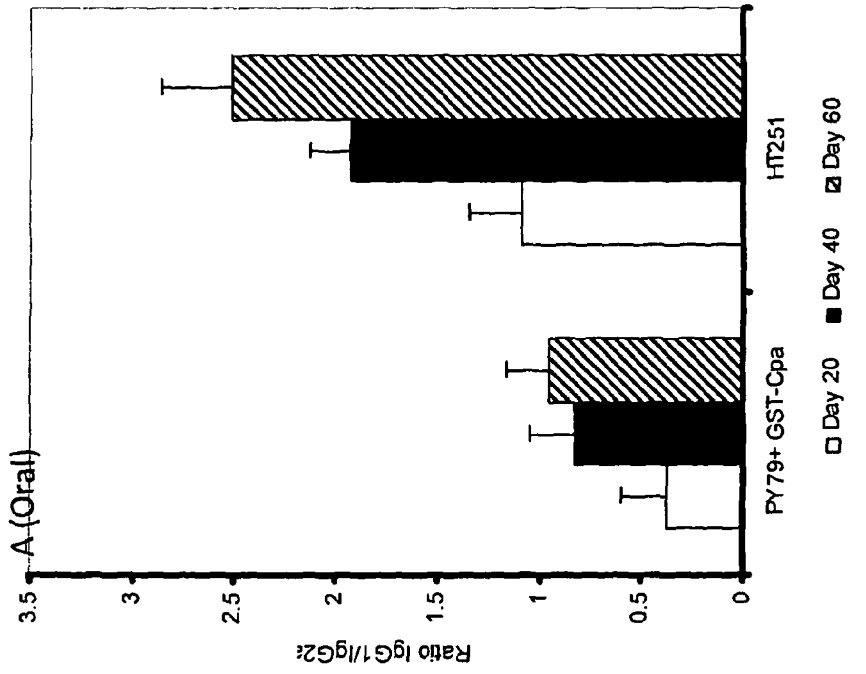
Figure 12B:
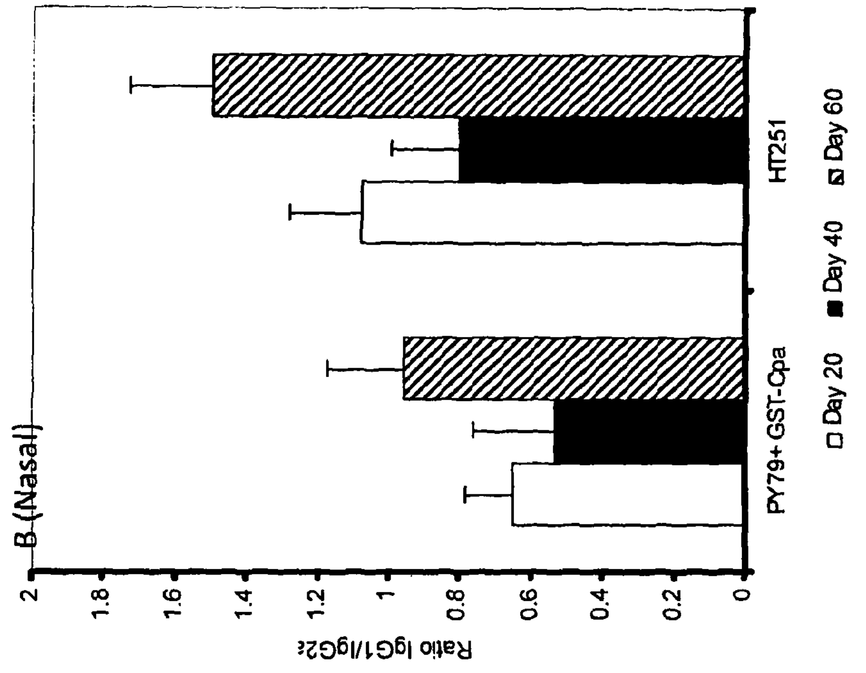
Figure 12C:
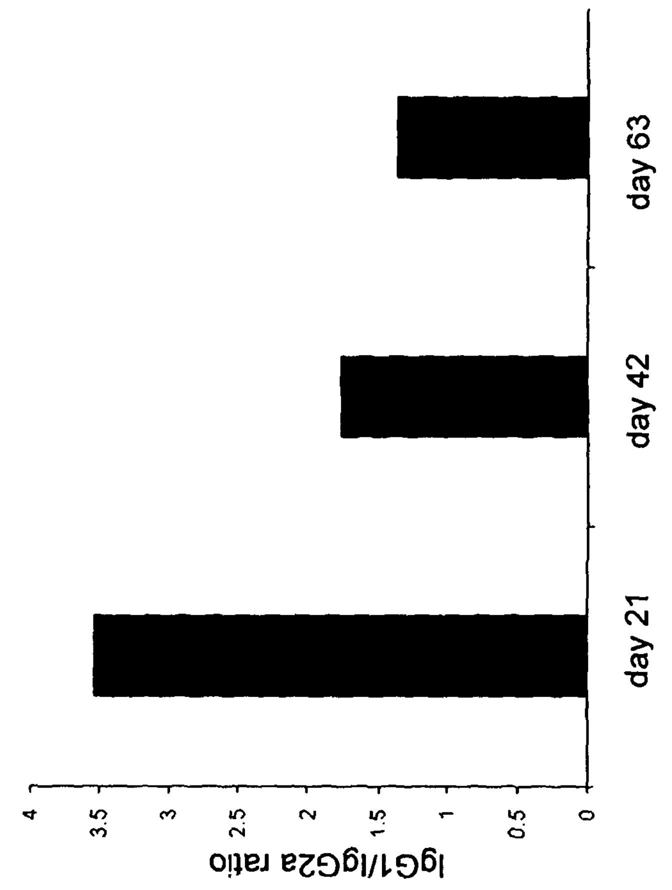
Figure 12D:
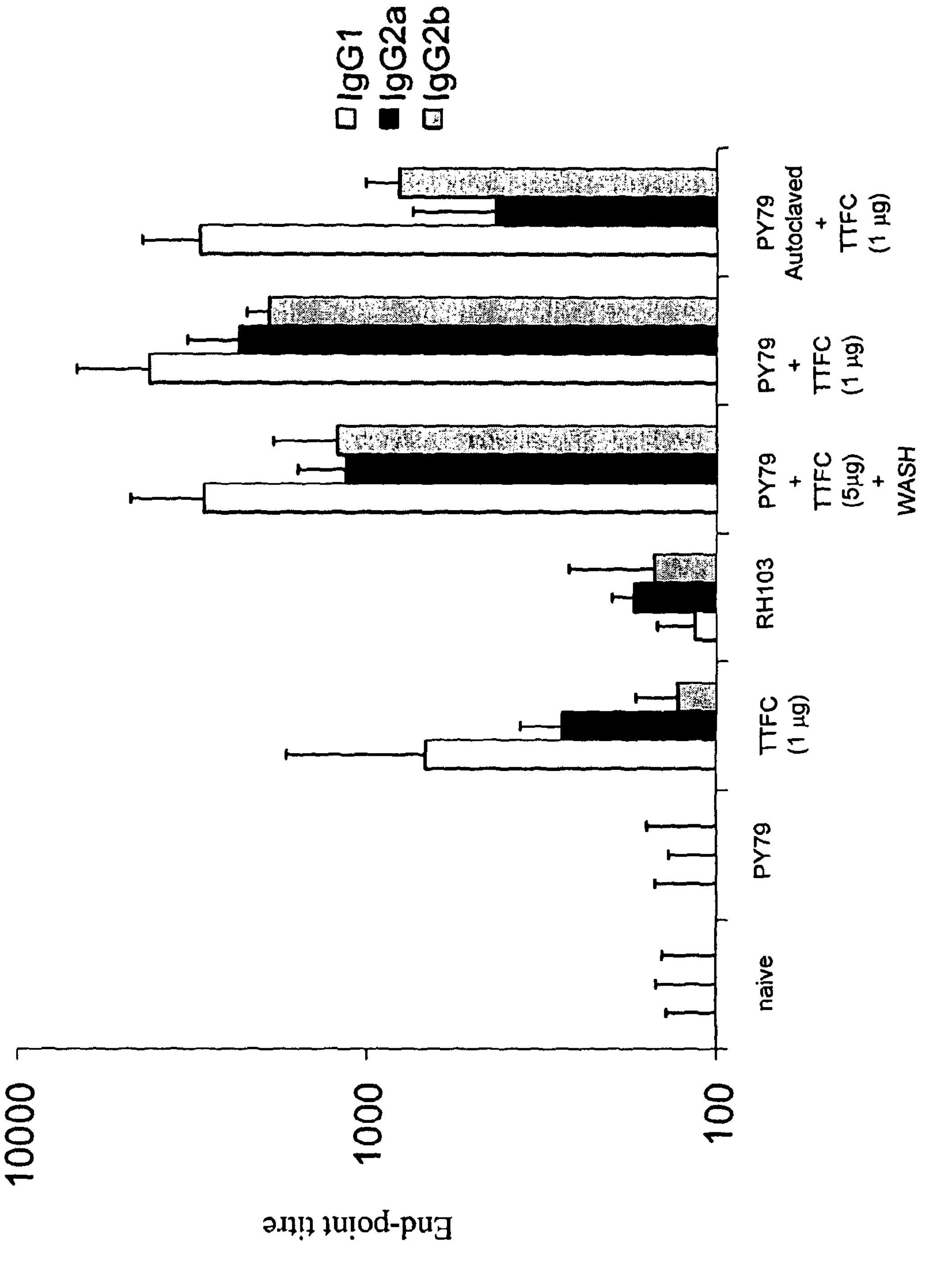

The Broad Spectrum of Immune Responses Produced Following Administration of Preadsorbed Spores The range of immune responses obtained in mice immunised with spores pre-adsorbed with GST-$Cpa_{247-370}$ (FIGS. 11A and 11B), TTFC (FIG. 11C) or PA (FIG. 11D) were examined in detail. Serum from mice dosed with pre-adsorbed spores in each case seroconvert with high levels of antigen-specific IgG at levels significantly ($P<0.05$) greater than control groups including those dosed with protein alone. Analysis of isotypes and specifically, the increase in the IgG1:IgG2a, indicated a $T_H2$ bias for GST-$Cpa_{247-370}$-specific humoral responses (FIGS. 12A and 12B). For PA-adsorbed spores a decrease in PA-specific IgG1:IgG2a ratios was observed suggesting a $T_h1$ bias which was supported by a potent induction in PA-specific IFN-γ production (FIG. 12C). For TTFC levels of both IgG2a and IgG2b were equivalent (FIG. 12D) yet IFN-γ was induced in stimulated splenocytes (in agreement on previous studies on TTFC-specific cellular responses (Mauriello et al., 2007)), which could indicate a balanced $T_H1$-$T_H2$ response.

Antigen-specific secretory IgA (sIgA) was also produced in the lungs, saliva and faeces (FIGS. 13A to C) demonstrating the induction of mucosal responses as well as systemic (i.e., IgG). Finally, as a clear indication of cellular responses and a $T_H1$ bias, IFN-γ production (FIG. 14), was strongly induced in mice dosed with PY79 spores adsorbed with TTFC or PA protein (IFN-γ was not tested in mice immunised with spores adsorbed with GST-$Cpa_{247-370}$). Taken together, spores preadsorbed with antigen could generate a broad range of responses, humoral (mucosal and systemic) and cellular, a characteristic desirable for effective vaccination.

Discussion

Bacterial spores have been shown to have utility as recombinant vaccine vehicles where an antigen is expressed on the spore surface or within the germinating spore. As such, spores offer the added advantage of their unique heat-stability and lend themselves to specific applications such as traveller's vaccines or for use in developing countries. As with all recombinant bacterial vaccines there also exist additional concerns over the use of genetically modified microorganisms. This work demonstrates a specific and novel application of bacterial spores where an antigen can be immobilised on the spore surface and when delivered generates a broad range of immune responses. More than just stimulating immune responses this approach has been shown to confer protection using two challenge models and a third by inference from the levels of neutralising antibodies. As such, spores have the ability to act as adjuvants without the need for genetic modification.

The single most important concern in the development of adjuvants is safety and for this reason, alum has remained the only adjuvant licensed for human use. *Bacillus spores*, including *B. subtilis*, are being widely used as dietary supplements (i.e., probiotics) with a number of species registered for human use, including *B. subtilis, B. cereus, B. clausii* and most recently, *B. coagulans*, that has received GRAS status from the US Food and Drug Administration. Together with the fact that killed spores can be used as effectively as live spores for vaccination strongly supports their consideration as safe adjuvants. The inventors proof-of-principle studies have used the nasal route of administration yet that we have also shown that oral delivery can be considered, especially when appropriate protective coating/excipients are used to protect the therapeutic agent. The size of spores (length of 0.8-1.5 nm depending on species) most closely aligns them with particulate adjuvants where an exogenous antigen displayed on a surface structure closely mimics a potential pathogen in both size and appearance (Raychaudhuri et al., 1998). Such particulate adjuvants are easily taken up by antigen presenting cells (APCs) and can induce potent immune responses (Singh et al., 1999). Studies have shown that exogenous antigens displayed in this way are presented 1000-10,000 times more efficiently by MHC (major histocompatibility complex) molecules through the class I and class II pathways compared to the soluble antigen alone (Hording et al., 1994; Kovacsorics-Bankowski et al., 1993). The broad range of humoral, local and cellular responses observed with immunisation with adsorbed spores are highly desirable in vaccines. The high titres of IgG2a and IFN-γ production are indicative of $T_H1$ biased immune responses and the recognition of conformational epitopes (Snapper et al., 1987). Studies on copolymer adjuvants have lead to the proposal that it is essential to maintain the native conformation of the immunogen to generate protective immunity (Hunter 2002). Other than the levels of protection achieved in this work the inventors have compelling evidence that proteins that bind to the spore can maintain their native conformation. This arises from studies where they have bound alkaline phosphatase to the spore (at pH 4) and shown that full enzyme activity is retained (unpublished data). This phenomenon has obvious applications for enzyme delivery.

Orally administered spores are taken up by M cells and enter the Peyer's patches where they would be expected to be taken up by APCs (Duc et al., 2003; Rhee et al., 2004). The inventors predict that adsorbed spores will also enable delivery of antigens using the same route. It is important to note that recombinant spores also promote the same spectrum of immune responses as adsorbed spores except that with the latter greater amounts of antigen can be loaded per spore. For example, with TTFC, a single intra-nasal dose of recombinant spores will deliver 0.2 μg of immunogen compared to 1 μg using spore adsorption. In addition, adsorbed spores enable antigens to be adsorbed that ordinarily cannot be expressed on the spore surface, for example, the inventors have succeeded in adsorbing the CSP antigen from *Plasmodium berghei* on the spore which otherwise cannot be expressed (unpublished data).

An important aspect of protein adsorption to spores is that it is enhanced at low pH. As the pH falls below the isolectric point the protein, now carrying a net positive charge would bind to the still negatively charged spore using electrostatic interactions. At pH values above the isoelectric point both protein and spore would be negatively charged thus explaining why binding was minimal or non-existent. One exception, of course, was binding of GST-$Cpa_{247-370}$, which will be discussed later. Adsorption was noticeably enhanced in the presence of salt and at high ionic strengths adsorption actually increased. The phenomena has been documented for the adsorption of poliovirus at low pH to membrane filters where both electrostatic and hydrophobic interactions play a role in virus binding (Shields et al., 1983). In the virus study salt (NaCl or $MgCl_2$) was shown to enhance hydrophobic interactions and at high ionic strengths (>0.3M) NaCl could only disrupt electrostatic interactions if hydrophobic interactions were also disrupted. In the present work the inventors have shown that treating adsorbed spores with a combination of salt and detergent was most effective at removing a bound protein. This suggests a combination of electrostatic and hydrophobic interactions are responsible for binding.

Following binding little dissociation was observed even after resuspension of adsorbed spores in a buffer of higher pH. This stability is important and clearly contributes to the adjuvant effect where spores would encounter the mucus of the nasopharanyx that has a neutral pH. By contrast, oral delivery should further enhance adsorption of antigen to spore but is unable to protect it from the enzymes present in gastric juices in the absence of a protective coat.

In data not shown the inventors have also demonstrated that a number of other immunogens can bind to the spore in a pH-dependant manner, including, *Clostridium difficile* toxin A, listeriolysin from *Listeria monocytogenes* and the CSP protein of *Plasmodium berghei*. The one exception was GST-$Cpa_{247-370}$ that although exhibiting strongest binding at low pH, it also bound at a pH greater than its isoelectric point (5.7). It is possible that the GST or Cpa moieties of the chimeric protein fail to adsorb to the spore in their native form and this may explain the resulting $T_H2$-biased immune response.

The surface coat of *B. subtilis* spores is well characterised and consists of about forty different protein species (Henriques et al., 2007). Spores of most species of *Bacillus* species also carry a well-developed exosporium, a loose fitting glycosylated envelope that encases the spore coat in a sac-like structure. Evidence now emerging has shown that *B. subtilis* carries a primitive exosporium (Waller et al., 2004) which may be more apparent in natural isolates of *B. subtilis* and has been observed in spores of HU58 here (Hong et al., 2009). What contributes to the net negative charge at low pH is unclear since at this pH carboxylic groups will be fully protonated.

The binding phenomena of spores at low pH is equally relevant at high pH where the spore would become more negatively charged and able to bind positively charged molecules. This application is already being developed for heavy metal adsorption and recovery (He et al., 1998, Daughney et al., 2001; Pang et al., 2005). Other applications apparent from this study are in the adsorption of small peptides, biotherapeutic molecules and as mentioned earlier, enzymes. A number of studies have shown that orally administered spores can suppress symptoms caused by toxin-producing bacteria, including *Escherichia coli* 070:K80, *Salmonella enterica* serotype Enteritidis, *Clostridium perfringens* and *Citrobacter rodentium* (La Ragione et al., 2003; La Ragione et al., 2001; D'Arienzo et al., 2006). The spores of the present invention can be used as vaccine formulations providing a simple, yet effective, tool for boosting and manipulating immune responses.

TABLE 1

Protection against challenge with alpha-toxin and tetanus toxin in immunised mice.

Alpha toxin challenge experiments[a]

| Group | Route | Dose of alpha toxin ($LD_{50}$) | No. survivors | Mean time to death ± (h) |
|---|---|---|---|---|
| naive | — | 2 | 0/4 | 4.5 ± 0.5 |
| PY79 spores | oral | 6 | 0/6 | 2.0 ± 0.5 |
| 3.6 μg GST-$Cpa_{247-370}$ | oral | 6 | 0/6 | 2.5 ± 0.5 |
| PY79 spores + | oral | 6 | 1/6 | — |
| 3.6 μg GST-$Cpa_{247-370}$ | | 12 | 0/6 | — |
| HT251 | oral | 6 | 6/6 | — |
| (cotB-GST-$Cpa_{247-370}$) | | 12 | 3/6 | — |
| PY79 spores | intra-nasal | 6 | 0/6 | 2.0 ± 0.5 |
| 0.15 μg GST-$Cpa_{247-370}$ | intra-nasal | 6 | 0/6 | 2.5 ± 0.3 |
| PY79 spores + | intra-nasal | 6 | 5/6 | — |
| 0.15 μg GST-$Cpa_{247-370}$ | | 12 | 0/6 | |
| HT251 (cotB-GST-$Cpa_{247-370}$) | intra-nasal | 6 | 6/6 | — |

Tetanus toxin challenge experiments[b]

| Group | Route | pH[c] | Toxin challenge dose ($LD_{50}$) | No. of survivors/ total |
|---|---|---|---|---|
| naive | — | — | 2 | 0/10 |
| PY79 spores | intra-nasal | 7 | 2 | 0/3 |
| | | | 50 | 0/7 |
| 1 μg TTFC protein | intra-nasal | 4 | 50 | 0/9 |
| RH103 spores (CotB-TTFC) | oral | 7 | 20 | 1/10 |
| PY79 spores + 5 μg TTFC protein then washed[d] | intra-nasal | 4 | 50 | 8/10 |
| PY79 spores + 1 μg TTFC protein | intra-nasal | 4 | 50 | 9/10 |
| Autoclaved PY79 spores + 1 μg TTFC protein | intra-nasal | 4 | 50 | 5/10 |

[a]Mice were immunised with PY79 spores, GST-$Cpa_{247-370}$ protein or PY79 spores adsorbed with GST-$Cpa_{247-370}$ protein by the oral or intra-nasal routes using dosings on days 1, 21 and 42. A challenge on immunised animals using alpha toxin was conducted 63 days after the start of the dosing regime. A control group received recombinant HT251 spores that expressed GST-$Cpa_{247-370}$ on the spore coat as a fusion to the coat protein CotB.

[b]Groups of mice immunised were immunised with PY79 spores that had been pre-adsorbed with recombinant TTFC protein. Variations included the use of autoclaved spores or pre-adsorption followed by washing of the spore. After nine doses on day 63 animals were challenged (sub-cutaneously) with tetanus toxin. Individuals showing no symptoms after 14 days were considered immune.

[c]refers to the pH of the PBS with which spores or protein was administered to animals.

[d]spores and protein pre-adsorbed (1 h, RT) in PBS buffer at pH 4, followed by two washes in PBS (pH 4).

EXAMPLE 3

Spore Preparation

Spores were prepared as described above with respect to Example 1. In particular, spores used for antigen binding were pre-treated with lysozyme (20 mg/ml), NaCl (1M) and KCL (1M). Spore crops were first incubated for 30-60 minutes in PBS (pH 7.4) or a similar buffer containing lysosyme. Next, spores are centrifuged and washed 1-2 times each with KCl and then NaCl.

A suspension (~$10^{10}$ cfu/ml) of treated spores (as mentioned above) were autoclaved at 121° C. for 20 minutes. Before the binding experiment autoclaved spores were washed once with 10-times PBS (0.1 M; pH7.4) then followed by washing 3 times with PBS (0.01M, pH7.4). All washing steps comprised centrifugation at room temperature (14,000 rpm for 1-2 minutes) to pellet the spores.

Adsorption of Inactivated Virus (H5N1) to Spores

Spores are counted before autoclaving by a viable count method on agar plates, and this should also be confirmed by direct counting using a counting chamber (e.g., a haeomcytometer) and phase contrast microscopy. First, calculate the number of washed and treated spores (cfu) needed for immunisation or other purpose. Transfer the spore suspension (with the quantity of spores needed) into "low binding" plastic centrifuge tubes (Eppendorf or similar), pellet spores by centrifugation, then resuspend the pellet in PBS (0.01M, pH7) containing the inactivated virus (for H5N1: calculate 1.2 μg HA per $1\times10^9$ spores/mouse) in a volume sufficient for one immunisation. Shake gently using an orbital shaker at RT for 30 minutes. The inactivated H5N1 virus was inactivated by treatment with formaldehyde. In particular, the NIBRG-14 inactivated virus obtained from NIBSC was used.

Laser scanning confocal microscopy was used to confirm that the H5N1 virus was bound on individual spores (data not shown).

Mice were dosed nasally with autoclaved *B. subtilis* spores adsorbed with formaldehyde inactivated H5N1 (on days 1, 2, 3, 6 and 27 using $2\times10^9$ spores adsorbed with 1.2 μg HA (haemagglutin protein) of H5N1). A variety of controls were also tested.

Results

The inventors looked at the level of HA IgA in the saliva and the lungs of the mice. The spores having the adsorbed H5N1 inactivated virus produced high levels of HA IgA. In particular, substantially greater levels than that achieved using just a mixture of the inactivated virus and the spores (data not shown). This data is considered to show that a local or mucosal immune response is generated in response to the spores having the adsorbed H5N1 inactivated virus.

FIG. 15 shows the ratio of IgG1 to IgG2a in blood samples taken from the mice. The low ratio achieved using the spores having the adsorbed H5N1 inactivated virus compared to the high ratio obtained using Alum in combination with the inactivated H5N1 virus shows clearly that the spores confer a Th1 biased immune response. This is highly desirable in virus vaccine formulations.

Mice were vaccinated via the intranasal route on days 1 and 14 with the spores having the adsorbed H5N1 inactivated virus. On day 42 the mice were challenged with either H5N1 strain A/Vietnam/119/04 or A/Turkey/1/2005. The number of responders that produce a HA titer of greater that 160 is shown in Table 2 below. The use of the spores having the adsorbed H5N1 inactivated virus produced the best immune response indicating that the spores having the adsorbed H5N1 inactivated virus provide the best protection.

TABLE 2

| | No. of responder[a] (percentage) | GMT of responders | No. of responders[a] (percentage) | GMT of responders |
|---|---|---|---|---|
| naive | 0 (0%) | 0 ± 0 | 0 (0%) | 0 ± 0 |
| PY79 spores | 0 (0%) | 0 ± 0 | 0 (0%) | 0 ± 0 |
| Autoclaved | 0 (0%) | 0 ± 0 | 0 (0%) | 0 ± 0 |
| PY79 spores H5N1 | 1 (20%) | 88 ± 44 | 0 (0%) | 72 ± 18 |
| PY79 spores + H5N1 | 5 (83%) | 227 ± 106 | 6 (100%) | 293 ± 65 |
| Autoclaved PY79 spores + H5N1 | 6 (100%) | 187 ± 65 | 5 (83%) | 200 ± 98 |
| Alum + H5N1 | 4 (67%) | 207 ± 130 | 2 (33%) | 133 ± 97 |

Discussion

The data shows that virus can be adsorbed onto the spores and that spores with the adsorbed virus can be used as a vaccine to provide protection against subsequent viral challenge.

The inventors have additionally administered spores (subcutaneously) and inactivated H5N1 virions (nasally) to mice and compared the antibody titers produced with those produced by nasal dosing of mice with spores adsorbed with the virus. All immunisations are performed at exactly the same time and the dose and regimen are as described above.

The data shows that adsorption confers stronger immune responses than if spores and immunogen are dosed by separate routes (data not shown).

H5N1 virus being an enveloped virus would be expected to adsorb to the surface of spores by virtue of hydrophobic interactions between the viral envelope and the spore surface. In the case of the latter, treatment under low pH conditions will help deprotonate the spore coat and render it more accessible to binding to virus, first by the effect of low pH on increasing hydrophobic binding and 2) by exposing hydrophobic domains of partially unfolded proteins on the spore coat. Both principles are not mutually exclusive and may work together to increase and enhance virus-spore interactions.

EXAMPLE 4

Adsorption of Paclitaxel (Taxol)

Paclitaxel is an anti-cancer chemical which specifically binds on alpha subunit of tubulin, thereby stabilizing microtubules and as a result, interferes with the normal breakdown of microtubules during cell division. It is used through intravenous transfusion for treatment of patients having breast cancer, certain types of cancer in lung, ovarian, colon, head and neck cancer, and advanced forms of Kaposi's sarcoma.

Following the method described above in example 3, the inventors have adsorbed spores with the hydrophobic anticancer chemical paclitaxel. The spores can thus be used as adjuvant for drug delivery to cancer cells.

Fluorescent labeled paclitaxel-Oregon Green (ex/em: 488 nm/525 nm) was bound to living and dead spores of *B. subtilis* PY79 in physiological phosphate saline buffer pH 7.4. Under this condition, both living and dead (autoclaved) spores could adsorb stably paclitaxel-Oregon as indicated by bright green signal of paclitaxel-Oregon on every individual spores (data not shown). No fluorescent signal could be detected in negative control, natural spores without paclitaxel-Oregon incubation.

Paclitaxel-Oregon and paclitaxel-bound spores where incubated with HCT-116 colorectral cancer cells for 4 hours. The results demonstrate the ability of spores to quickly concentrate paclitaxel onto the cancer cells, and that paclitaxel did not quickly become detached from the spores but was released slowly over the 4 hours to bind to the cancer cells (see FIG. 16).

The administration of paclitaxel coated *B. subtilis* spores provided a 4-fold increasing of paclitaxel binding into colorectal cancer cells. Further analysis of the kinetics of cell-targeting of spores and chemical release from spores together with cell-killing activity assay should contribute to further developing an effective and slow-release formulation.

EXAMPLE 5

Adsorption of *Clostridium difficile* Toxins

*Clostridium difficile* is the most common cause of noscomial antibiotic-associated diarrhea in developed countries. Antibiotic therapy and disruption of the normal gastrointestinal microflora are the primary causes of *C. difficile*-associated disease (CDAD) and one or both of these factors are a prerequisite for colonization of the gut by this Gram-positive bacterium. Morbidity and mortality rates have been steadily increasing in recent years and probably result from the emergence of more virulent strains of *C. difficile* as well as the changing patterns of antibiotics usage. Recent estimates of CDAD in the USA suggest as many as 500,000 cases per year with up to 20,000 mortalities. CDAD is caused by the secretion of two exotoxins, toxin A and toxin B, both monoglucosyltransferases that are cytotoxic, enterotoxic and proinflammatory. CDAD is particularly problematic to treat and to contain because of the ability of this bacterium to form robust endospores that can persist and be easily transferred in a hospital environment. Currently, the only treatment is the use of antibiotics such as vancomycin and metradinazole and a parenteral anti-toxoid vaccine is under clinical evaluation.

An effective vaccine to CDAD should target the two principal virulence factors, toxin A and toxin B since anti-toxin A and anti-toxin B antibodies correlate well with protection in both hamsters and humans. Toxin B is considered of greater importance for CDAD than toxin A where, using a hamster model of infection, mutants in the tcdA gene that encodes toxin A were shown to retain full virulence. Despite this a possible role for toxin A in CDAD has not been excluded. The tcdA and tcdB genes that encode toxin A and toxin B respectively both carry extensive homology and particularly at the C-termini where each carries an elaborate array of repeated domains. These domains are involved in initial binding of the toxin prior to its translocation across the endosmomal membrane. Antibodies specific to the C-terminal ligand binding domain should be neutralizing and in the case of toxin A, a C-terminal segment referred to as 14CDTA has been used in a recombinant *Salmonella* vaccine and shown to elicit local and systemic immunity and anti-toxin A neutralizing activity.

Adsorption of C-Terminal Domains Onto Non-Recombinant Spores

The inventors adsorbed 14CDTA and $Tcd_{15-24}$ onto the spore surface in PBS buffer at pH 4.0. Using wild type, autoclaved, PY79 spores, 14CDTA was mixed with pure suspensions of spores ($1\times10^{10}$) using the methods described above, and the coated spores retained. The peptides were present in spore coat protein extracts and binding was robust and both electrostatic and hydrophobic in nature being able to resist washing with NaCl and detergent. Approximately 6 µg of 14CDTA was bound to $1\times10^{10}$ spores.

The coated spores were administered to Golden Syrian hamsters on days 1, 8, 36, 43 and 50. The hamsters were protected against a subsequent challenge with *Clostridium difficile* in 80% of cases. Accordingly, the 14CDTA coated spores provides immunological protections against *Clostridium difficile.*

EXAMPLE 6

Adsorption of *Plasmodium berghei* CSP Protein

CSP is the circumsporozoite protein from *Plasmodium berghei* and is critical for sporozoite function and invasion of hepatocytes. It is also a major Malaria vaccine candidate antigen.

Recombinant CSP protein was adsorobed onto autoclaved *B. clausii* spores using the methods described above. *Bacillus clausii* strain O/C is the strain of *B. clausii* that is contained within the commercial product known as Enterogermina. Enterogermina is manufactured by Sanofi-Aventis and is a licensed OTC medicine designed to prevent infantile diarrhoea (rotavirus infection). Mice were then immunized by a parenteral route (intra-peritoneal) using the coated spores.

A moderate cellular response and strikingly high anti-CSP IgG titres were observed in vaccinated animals. Furthermore, In vitro experiments clearly demonstrated the sporozoite neutralizing capacity of sera obtained from these mice.

Vaccinated mice were challenged by i.v. injection of 1000 *P. berghei* sporozoites into the tail vein. Under these conditions, vaccination prevented parasitaemia (see Table 3).

Taken together administration of recombinant CSP coated *B. clausii* spores turned out to elicit anti-plasmodial immune responses, especially a remarkably high humoral response. Thus, this vaccination regimen could contribute, either alone or in combination with other vaccination schemes, to the development of an efficient pre-eryhrocytic malaria vaccine.

TABLE 3

| Group | immunisation | No. protected mice/total number of mice | % PROTECTION | Prepatency period (days) |
|---|---|---|---|---|
| A | Naïve | 0/5 | 0 | All mice (4) |
| B | O/C | 0/5 | 0 | 4 mice (4)<br>1 mouse (5) |
| C | Csp | 0/5 | 0 | All mice (4) |
| D | O/C + CSP | 3/5 | 60 | 1 mouse (4)<br>1 mouse (6)<br>3 mice (-0) |

All documents cited in the application are incorporated herein by reference.

REFERENCES

1. Detmer, A. & Glenting, J., *Microb Cell Fact,* 5, 23 (2006).
2. Bumann, D. et al., *FEMS Immunol Med Microbiol.,* 27, 357-364 (2000).
3. Hong, H. A. et al., *FEMS Microbiology Reviews,* 29, 813-835 (2005).
4. Due, L. H. et al., *Infection and Immunity,* 71, 2810-2818 (2003).
5. Hoang, T. H. et al., *Infect Immun.,* 76, 5257-5265 (2008).
6. Duc, L. H. et al., *Vaccine,* 25, 346-355 (2007).
7. Zhou, Z. et al., *Vaccine,* 26, 1817-1825 (2008).
8. Singh, M. et al., *Nat. Biotechnol.,* 17, 1075-1081 (1999).
9. Moyle, P. M. et al., *Curr. Drug. Deliv.,* 1, 385-396 (2004).
10. Maloy, K. J. et al., *Immunology,* 81, 661-667 (1994).
11. Hunter, R. L., *Vaccine,* 20 Suppl 3, S7-12 (2002).
12. Malkiel et al., J. Allergy Clin. Immunol., 48, 220-223 (1971).
13. Williamson, E. D. & Titball, R. W., *Vaccine,* 11, 1253-1258 (1993).
14. Barbosa, T. M. et al., *Applied and Environmental Microbiology,* 71, 968-978 (2005).
15. Seale, R. B. et al., *Appl. Environ. Microbiol.,* 74, 731-737 (2008).
16. Ahimou, F. et al., *Bacillus subtilis. J. Microbiol. Methods,* 45, 119-126 (2001).
17. Shields, P. A. et al., *Appl. Environ. Microbiol.,* 45, 526-531 (1983).
18. Fairweather, N. F. et al., *Escherichia coli. Infection and Immunity,* 55, 2541-2545 (1987).
19. Duc, L. H. et al., *Vaccine,* 25, 346-355 (2007).
20. Flick-Smith, H. C. et al., *Infect. Immun.,* 70, 2022-2028 (2002).
21. Flick-Smith, H. C. et al., *Infect. Immun.* 70, 1653-1656 (2002).
22. Tam, N. M. K. et al., *Journal of Bacteriology,* 188, 2692-2700 (2006).
23. Mauriello, E. M. et al., *Vaccine,* 25, 788-793 (2007).
24. Raychaudhuri, S et al., *Nat. Biotechnol.,* 16, 1025-1031 (1998).
25. Harding, C. V., et al., *J. Immunol.,* 153, 4925-4933 (1994).
26. Kovacsovics-Bankowski, M., et al., *Proc. Natl. Acad. Sci. U S A,* 90, 4942-4946 (1993).
27. Snapper, C. M. et al., *Science,* 236, 944-947 (1987).
28. Rhee, K. J. et al., *Journal of Immunology,* 172, 1118-1124 (2004).
29. Henriques, A. O. et al., *Annu. Rev. Microbiol.,* 61, 555-588 (2007).
30. Waller, L. N. et al., *J. Microbiol. Methods,* 58, 23-30 (2004).
31. Hong, H. A. et al., *Res. Microbiol.,* 160, 134-143 (2009).
32. He, L. M. et al., *Appl. Environ. Microbiol.,* 64, 1123-1129 (1998).
33. Daughney, C. J. et al., *Geochimica et Cosmochimica Acta,* 65, 1025-1035 (2001).
34. Pang, L. et al., *J. Environ. Qual.,* 34, 237-247 (2005).
35. La Ragione, et al., *Veterinary Microbiology,* 94, 245-256 (2003).
36. La Ragione, et al., *Veterinary Microbiology,* 79, 133-142 (2001).
37. D'Arienzo, R. et al., *Res. Microbiol.,* 157, 891-897 (2006).
38. Youngman, P. et al., *Plasmid,* 12, 1-9 (1984).
39. Isticato, R. et al., *Journal of Bacteriology,* 183, 6294-6301 (2001).
40. Nicholson, W. L. & Setlow, P. in Molecular Biological Methods for *Bacillus*. (eds. C. R. Harwood. & S. M. Cutting.) 391-450. (John Wiley & Sons Ltd., Chichester, UK.; 1990).
41. Sze, A. et al., *Journal of Colloid and Interface Science,* 261, 402-410 (2003).
42. Walker, J. et al., *Mol. Biochem. Parasitol,* 61, 255-264 (1993).
43. Uyen, N. Q., et al., *Vaccine,* 25, 356-365 (2007).
44. Lee M. He, et al., *Appl. Environ. Microbiol.* 64: 1123-1129 (1997).
45. Tilton R. et al., *Langmuir,* 7, 2710-2718 (1991).
46. Bisheuvel, P. et al., *J. Phys. Chem. B.,* 108: 17660-17665 (2004).
47. Daughney, C. et al., *Geochim. Cosmochim. Acto.,* 65: 1025-1035 (2000).
48. Zhang Z. et al., *Colloids and Surfaces B: Biointerfaces,* 34: 113-121 (2003).
49. Yitzhaki S. et al., *Anal. Chem.,* 78: 6670-6673 (2006).
50. Yee N. et al., *Geochimica et Cosmochimica Acta.,* 64: 609-617 (1999).
51. Small D. et al., *Applied and Environmental Microbiology.,* 52: 220-223 (1986).

The invention claimed is:

1. A method of adsorbing a therapeutic agent onto a bacterial spore comprising:

mixing the spores and the therapeutic agent at a pH that is less than or equal to the isoelectric point of the therapeutic agent, and under low salt concentration conditions where the hydrophobic interactions between the spores and the therapeutic agent are enhanced, wherein the therapeutic agent is selected from the group consisting of: proteins, denatured viruses or other infectious agents, receptor agonist proteins, and receptor antagonist proteins.

2. The method of claim 1, wherein the spore is a *Bacillus* or a *Clostridium* spore.

3. The method of claim 1, wherein the spore is a *Bacillus* spore.

4. The method of any one of the preceding claims, wherein the spore is denatured so that germination is prevented.

5. The method of claim 1, wherein a plurality of different therapeutic agents are adsorbed onto the spore.

6. The method of claim 1, wherein the therapeutic agent is linked to a modifying agent.

7. The method of claim 1, wherein the pH is less than 7.

8. The method of claim 1, wherein the pH is less than 5.

9. The method of claim 1, wherein the pH is about 4 or less.

10. The method of claim 1, wherein the pH is above the Zero Point of Charge (ZPC) of the spore.

11. The method of claim 1, wherein the pH is above pH 2.

12. The method of claim 1, wherein the low salt concentration is less than 0.3M.

13. The method of claim 1, wherein the spore and the therapeutic agent are mixed together in a binding solution, wherein the pH of the binding solution is less than or equal to the isoelectric point of the therapeutic agent and has a salt concentration of less than 0.3M.

14. The method of claim 12, wherein the low salt concentration is less than 0.15M.

15. The method of claim 1, additionally comprising formulating the spores with the adsorbed therapeutic agent as a pharmaceutical composition by combining with one or more pharmaceutically acceptable carriers or vehicles.

16. The method of claim 15, wherein the pharmaceutical composition is an immunogenic composition.

17. The method of claim 16, wherein the method additionally comprises adding an adjuvant.

18. The method of claim 1, wherein the therapeutic agent is an antigen.

19. The method of claim 18, wherein the antigen is derived from one or more infectious agents selected from the following group:

HIV, Hepatitis A, Hepatitis B, influenza viruses (orthomyoxviruses), Herpes viruses, papovaviruses, Rhabdoviruses, vesicular stomatitis virus (VSV), *Escherichia* spp. including *E. coli* and ETEC (enterotoxigenic *E. coli*), *Legionella* spp., *Bacillus* spp., *Neisseria* spp., *Haemophilus* spp., *Helicobacter* spp., *Corynebacterium* spp., *Pneumococcus* spp., *Salmonella* spp., *Mycobacterium* spp., *Chlamydia* spp. and *Shigella* spp. including 5. dysenteriae, *S. sonnei* and *S. flexneri, Cryptosporidium* spp., *Toxoplasma* spp., *Leishmania* spp., *Theilera* spp. and *Plasmodium* spp.

20. The method of claim 1 wherein the therapeutic agent is a protein, and the protein is selected from the group consisting of: an antigen, an enzyme, an antibody molecule, labile toxin from enterotoxigenic *E. coli* (ETEC), cholera toxin subunit B, tetanus toxoid, an anticancer protein.

21. The method of claim 1 wherein the therapeutic agent is a protein and the protein is selected from the group consisting of an infectious agent, a tumor antigen, and an allergen.

22. A method of adsorbing a therapeutic protein or peptide onto a bacterial spore comprising:

mixing the spores and the therapeutic protein or peptide at a pH that is less than or equal to the isoelectric point of the therapeutic protein or peptide, and under low salt concentration conditions where the hydrophobic interactions between the spores and the therapeutic protein or peptide are enhanced.

* * * * *